United States Patent
Katinger et al.

(10) Patent No.: US 7,494,659 B2
(45) Date of Patent: Feb. 24, 2009

(54) LIVE ATTENUATED INFLUENZA VACCINE

(75) Inventors: Hermann Katinger, Vienna (AT);
Andre Egorov, Vienna (AT); Boris Ferko, Wiener Neudorf (AT); Julia Romanova, Vienna (AT); Dietmar Katinger, Vienna (AT)

(73) Assignee: Polymun Scientific Immunbiologische Forschung GmbH (AT)

( * ) Notice: Subject to any disclaimer, the term of this patent is extended or adjusted under 35 U.S.C. 154(b) by 92 days.

(21) Appl. No.: 10/381,530

(22) PCT Filed: Sep. 25, 2001

(86) PCT No.: PCT/EP01/11087

§ 371 (c)(1),
(2), (4) Date: Oct. 3, 2003

(87) PCT Pub. No.: WO02/24876

PCT Pub. Date: Mar. 28, 2002

(65) Prior Publication Data

US 2004/0137013 A1    Jul. 15, 2004

(30) Foreign Application Priority Data

Sep. 25, 2000    (EP)    .................................. 00120896

(51) Int. Cl.
*A61K 39/145*    (2006.01)
*C12N 7/00*    (2006.01)

(52) U.S. Cl. ................ 424/206.1; 424/209.1; 435/235.1
(58) Field of Classification Search .............. 424/206.1, 424/209.1; 435/236, 239
See application file for complete search history.

(56) References Cited

U.S. PATENT DOCUMENTS 5,753,489 A * 5/1998 Kistner et al. ............ 435/235.1

FOREIGN PATENT DOCUMENTS

| WO | WO 99/64068 | 12/1999 |
|---|---|---|
| WO | WO 00/15251 | 3/2000 |

OTHER PUBLICATIONS

O. Kistner et al.: "Development of a Mammalian Cell (Vero) Derived Candidate Influenza Virus Vaccine", vol. 16, No. 9/10, 1998, pp. 960-968, XP002163941, see especially p. 961, paragraph bridging cols. 1 and 2.
O. Kistner et al.: "Development of a Vero Cell Derived Influenza Whole Virus Vaccine", Dev. Biol. Stand., vol. 98, 1999, pp. 101-110, XP000909542.
O.W. Merten et al.: "Production of Influenza Virus in Serum-free Mammalian cell Cultures", Dev. Biol. Stand., vol. 98, 1999, pp. 23-37, XP000990517.
N. Kaverin et al.: "Impairment of Multicycle Influenza Growth in Vero (WHO) Cells by Loss of Trypsin Activity", J. Virol., vol. 69, No. 4, 1995, pp. 2700-2703, XP002163942, cited in the application.

* cited by examiner

*Primary Examiner*—Stacy B. Chen
(74) *Attorney, Agent, or Firm*—Ostrolenk, Faber, Gerb & Soffen, LLP

(57) ABSTRACT

The invention relates to a simple and efficient process for isolating viruses from various sources and for producing live attenuated influenza vaccines in a serum-free Vero cell culture under conditions where alterations in the surface antigens of the virus due to adpative selection are minimized or prevented. The process does not require purification of the virus-containing supernatant harvested from the cell culture nor post-incubation treatment of the viruses for HA activation. The invention further relates to influenza A and B master strain candidates and to vaccines made thereof.

4 Claims, 1 Drawing Sheet

SEQUENCE LISTING

<160> NUMBER OF SEQ ID NOS: 37

<210> SEQ ID NO 1
<211> LENGTH: 2341
<212> TYPE: DNA
<213> ORGANISM: Influenza virus A/Singapore/1/57/ca

<400> SEQUENCE: 1

```
agcaaaagca ggtcaattat attcaatatg gaaagaataa aagaactacg gaatctgatg      60
tcgcagtctc gcactcgcga gatactaaca aaaccacag tggaccatat ggccataatt     120
aagaagtaca catcagggag acaggaaaag aacccgtcac ttaggatgaa atggatgatg     180
gcaatgaaat atccgattac agctgacaag aggataacag aaatgattcc tgagagaaat     240
gagcaagggc agactctatg gagtaaaatg aatgatgccg gatcggatcg agtgatggta     300
```

```
tcacctctgg ctgtgacatg gtggaataga aatggaccaa tgacaagtac ggttcattat      360
ccaaaaatct acaaaactta ttttgagaaa gtcgaaaggt taaaacatgg aacctttggc      420
cctgtccatt ttagaaacca agtcaaaata cgccgaagag ttgacataaa tcctggtcat      480
gcagacctca gtgccaagga ggcacaggat gtaatcatgg aagttgtttt ccctaacgaa      540
gtggggccca ggatactaac gtcggaatcg caattaacaa caaccaaaga gaaaaaagaa      600
gaactccagg attgcaaaat ttctcctttg atggttgcgt acatgttaga gagagaactt      660
gtccgaaaaa cgagatttct cccagttgct ggtggaacaa gcagtgtgta cattgaagtg      720
ttgcacttaa ctcaaggaac atgctgggaa cagatgtaca ctccaggtgg agaagtgagg      780
aatgatgatg ttgatcaaag tctaattatt gcagccagga catagtgag aagagcagca      840
gtatcagcag atccactagc atctttattg agatgtgcc acagcacaca gattggcggg      900
acaaggatgg tggacattct taggcagaac ccaacggaag agcaagctgt ggatatatgc      960
aaggctgcaa tgggactgag aatcagctca tccttcagtt ttggcgggtt cacatttaag     1020
agaacaagcg gatcatcagt caagatagag gaagaagtgc ttacgggcaa tcttcaaaca     1080
ttgaaaataa gggtgcatga gggatacgag gagttcacaa tggttgggaa aagggcaaca     1140
gctatactca gaaaagcaac caggagattg attcagctga tagtgagtgg aagagacgaa     1200
cagtcgatag ccgaagcaat aattgtggcc atggtatttt cacaagaaga ttgtatgata     1260
aaagcagtta gaggtgatct gaatttcgtt aataggcaa atcagcgatt gaatcccatg     1320
catcaacttt taagacattt tcagaaggat gcgaaagtgc ttttcaaaa ttggggaatt     1380
gaacatatcg acaatgtgat gggaatgatt ggggtattac agacatgac tccaagcaca     1440
gagatgtcaa tgagggggt aagagtcagc aaaatgggcg tagatgaata ctccagcgcg     1500
gagagagtag tggtgagcat tgaccggttt ttgagagttc gagaccaacg aggaaatgta     1560
ctactatctc ctgaggaggt cagtgaaaca caggaacaga gaaactgac aataacttac     1620
tcatcgtcaa tgatgtggga gattaatggc cctgagtcag tgttggtcaa tacctatcag     1680
tggatcatca gaaactggga aactgttaaa attcagtggt ctcagaatcc tacaatgcta     1740
tacaataaaa tggaatttga gccatttcag tctttagttc ctaaggccat tagaggccaa     1800
tacagtgggt ttgttaggac tctattccaa caaatgaggg atgtacttgg acatttgat     1860
accacccaga taataaaact tcttcccttt gcagccgccc caccaaagca agtagaatg     1920
cagttctctt cattgactgt gaatgtgagg ggatcaggaa tgagaatact tgtaaggggc     1980
aattctcctg tattcaacta caacaagacc actaagagac taacaattct cggaaaggat     2040
gctggcactt taactgaaga cccagatgaa ggcacatctg gagtggagtc cgctgttctg     2100
agaggattcc tcattctggg caaagaagat aggagatatg gaccagcatt aagcatcaat     2160
gaactgagta accttgcgaa aggagaaaag gctaatgtac taattgggca ggagacgtg     2220
gtgttggtaa tgaaacgaaa acgggactct agcatactta ctgacagcca gacagcgacc     2280
aaaagaattc ggatggccat caattaatgt tgaatagttt aaaaacgacc ttgtttctac     2340
t                                                                    2341
```

<210> SEQ ID NO 2
<211> LENGTH: 2341
<212> TYPE: DNA
<213> ORGANISM: Influenza virus A/Singapore/1/57/ca

<400> SEQUENCE: 2

```
agcaaaagca ggcaaaccat ttgaatggat gtcaatccga ccttactttt cttgaaagtt      60
ccagcgcaaa atgccataag tactacattc ccttatactg gagatcctcc atacagccat     120
ggaacaggaa caggatacac catggacaca gtcaacagaa cacatcaata ttcagaaaag     180
gggaagtgga caacaaacac ggaaactgga gcgccccaac ttaacccaat tgatggacca     240
ctacctgagg acaatgaacc aagtggatat gcacaaacag actgcgtcct ggaagcaatg     300
gctttccttg aagaatccca cccgggaatc tttgaaaact cgtgtcttga aacgatggaa     360
gttattcaac aaacaagagt ggacaaactg acccaaggtc gtcagaccta tgattggaca     420
ttgaacagaa atcagccggc tgcaactgcg ctagccaaca ctatagaggt cttcagatcg     480
aatggtctga cagctaatga atcgggaagg ctaatagatt tcctcaagga tgtgatagaa     540
tcaatggata aagaggagat ggaaataaca acacacttcc aaagaaaaag aagagtaaga     600
gacaacatga ccaagaaaat ggtcacacaa cgaacaatag aaaaaagaa gcaaagattg     660
aacaagagaa gctatctaat aagagcactg acattgaaca caatgactaa agatgcagag     720
agaggtaaat taagagaag agcaattgca acacccggta tgcagatcag agggttcgtg     780
tactttgtcg aaacactagc gagaagtatt tgtgagaagc ttgaacagtc tgggcttccg     840
gttggaggta atgaaaagaa ggctaaactg gcaaatgttg tgagaaaaat gatgactaat     900
tcacaagaca cagagctctc tttcacaatt actggagaca ataccaaatg gaatgagaat     960
caaaatcctc ggatgttcct ggcgatgata acatacatca aagaaatca acctgaatgg    1020
tttagaaacg tcctgagcat cgcacctata atgttctcaa ataaaatggc aagactaggg    1080
aaaggataca tgttcgaaag caagagcatg aagctccgaa cacaaatacc agcagaaatg    1140
ctagcaagta ttgacctgaa atactttaat gaatcaacaa gaaagaaaat cgagaaaata    1200
aggcctctcc taatagatgg cacagtctca ttgagtcctg aatgatgat gggcatgttc    1260
aacatgctaa gtacagtcat aggagtctca atcctgaatc ttggacaaaa gaagtacacc    1320
aaaacaacat actggtggga cggactccaa tcctctgatg acttcgccct catagtgaat    1380
gcaccaaatc atgagggaat acaagcagga gtggatagat tctacagaac ctgcaagcta    1440
gtcggaatca atatgagcaa aaagaagtcc tacataaata ggacagggac atttgaattc    1500
acaagctttt tctatcgcta tggatttgta gccaattta gcatggagct gcccagtttt    1560
ggagtgtctg gaattaatga atcggctgat atgagcattg gggtaacagt gataaagaac    1620
aacatgataa acaatgacct tgggccagca acagcccaaa tggctcttca actattcatc    1680
aaagactaca gatatacgta ccggtgccac agaggagaca cacaaattca gacaaggaga    1740
tcattcgagc taaagaagct gtgggagcaa acccgctcaa aggcaggact tttggtttcg    1800
gatggaggac caaacttata caatatccgg aatctccaca ttccagaagt ctgcttgaag    1860
tgggagctaa tggatgaaga ctatcagggg aggctttgta atcccctgaa tccatttgtc    1920
agtcataagg agattgagtc tgtaaacaat gctgtggtaa tgcccgctca cggtccagcc    1980
aagagcatgg aatatgatgc tgttgctact acacactcct ggatccctaa gaggaaccgc    2040
tccattctca acacaagcca agggggaatt cttgaggatg aacagatgta tcagaagtgt    2100
tgcaatctat tcgagaaatt cttccctagc agttcgtaca ggagaccagt tggaatttcc    2160
agcatggtgg aggccatggt gtctaggcc cggattgatg cacggattga cttcgagtct    2220
ggacggatta agaaagagga gttcgctgag atcatgaaga tctgttccac cattgaagag    2280
ctcagacggc aaaaatagtg aatttagctt gtccttcatg aaaaaatgcc ttgtttctac    2340
t                                                                    2341
```

<210> SEQ ID NO 3
<211> LENGTH: 2233
<212> TYPE: DNA
<213> ORGANISM: Influenza virus A/Singapore/1/57/ca

<400> SEQUENCE: 3

| | | | | | |
|---|---|---|---|---|---|
| agcaaaagca | ggtactgatc | cgaaatggaa | gattttgtgc | gacaatgctt | caatccgatg | 60 |
| attgtcgagc | ttgcggaaag | ggcaatgaaa | gagtatggag | aggatctgaa | aatcgaaaca | 120 |
| aacaaatttg | cagcaatatg | cactcacttg | gaagtatgct | tcatgtattc | agattttcat | 180 |
| ttcatcaatg | agcaaggcga | gtcaataata | gtagagcttg | atgatccaaa | tgcacttttg | 240 |
| aagcacagat | ttgaaataat | agagggaaga | gatcgcacaa | tggcctggac | agtagtaaac | 300 |
| agtatttgca | acactacagg | agctgagaaa | ccgaagtttc | tgccagattt | gtatgattac | 360 |
| aaggagaata | gattcatcga | gattggagtg | acaaggaggg | aagtccacat | atactatctt | 420 |
| gaaaaggcca | ataaaattaa | atctgagaag | acacacatcc | acattttctc | attcactggg | 480 |
| gaagaaatgg | ccacaaaggc | cgactacact | ctcgatgagg | aaagcagggc | taggatcaaa | 540 |
| accagactat | tcaccataag | acaagaaatg | gctagcagag | gcctctggga | ttcctttcgt | 600 |
| cagtccgaaa | gaggcgaaga | aacaattgaa | gaaagatttg | aaatcacagg | gacaatgcgc | 660 |
| aggctcgccg | accaaagtct | cccgccgaac | ttctcctgcc | ttgagatttt | tagagcctat | 720 |
| gtggatggat | tcgaaccgaa | cggctacatt | gagggcaagc | tttctcaaat | gtccaaagaa | 780 |
| gtaaatgcta | aaattgaacc | ttttctgaaa | acaacaccaa | gaccaattag | acttccggat | 840 |
| gggcctcctt | gttctcagcg | gtccaaattc | ctgctgatgg | atgctttaaa | attaagcatt | 900 |
| gaggacccaa | gtcacgaagg | agagggaata | ccactatatg | atgcgatcaa | gtgtatgaga | 960 |
| acattctttg | gatggaaaga | accctatgtt | gttaaaccac | acgaaaaggg | aataaatcca | 1020 |
| aattatctgc | tgtcatggaa | gcaagtactg | gcagaactgc | aggacattga | gaatgaggag | 1080 |
| aagattccaa | gaaccaaaaa | catgaagaaa | acgagtcagc | taaagtgggc | acttggtgag | 1140 |
| aacatggcac | cagagaaggt | agactttgac | gactgtagag | atataagcga | tttgaagcaa | 1200 |
| tatgatagtg | atgaacctga | attaaggtca | cttt caagct | ggatccagaa | tgagttcaac | 1260 |
| aaggcatgcg | agctgaccaa | ttcaatctgg | atagagctcg | atgagattgg | agaagatgtg | 1320 |
| gctccaattg | aacacattgc | aagcatgaga | aggaattact | tcacagcaga | ggtgtctcat | 1380 |
| tgcagagcca | cagaatatat | aatgaagggg | gtatacatta | atacagcctt | gcttaatgca | 1440 |
| tcctgtgcag | caatggacga | tttccaacta | attcccatga | taagcaaatg | tagaactaaa | 1500 |
| gagggaaggc | gaaagaccaa | tttatatggt | ttcatcgtaa | aaggaagatc | tcacttaagg | 1560 |
| aatgacaccg | acgtggtaaa | ctttgtgagc | atggagtttt | ctctcactga | cccaagactt | 1620 |
| gagccacaca | atgggagaa | gtactgtgtt | cttgagatag | gagatatgct | actaagaagt | 1680 |
| gccataggcc | aggtgtcaag | gcccatgttc | ttgtatgtga | ggacaaatgg | aacatcaaag | 1740 |
| attaaaatga | aatggggaat | ggagatgagg | cgttgcctcc | ttcagtcact | ccaacaaatc | 1800 |
| gagagcatga | ttgaagccca | gtcctctgtc | aaggagaaag | acatgaccaa | agagtttttc | 1860 |
| gagaataaat | cagaaacatg | gcccattgga | gagtccccta | aggagtggga | agaaggttcc | 1920 |
| attgggaagg | tctgcaggac | tttattagcc | aagtcggtat | tcaatagcct | gtatgcatct | 1980 |
| ccacaattag | aaggatttc | agctgaatca | agaaaactgc | tccttgtcgt | tcaggctctt | 2040 |
| agggacaatc | ttgaacctgg | gacctttgat | cttggggggc | tatatgaagc | aattgaggag | 2100 |

-continued

```
tgcctgatta atgatccctg ggttttgctt aatgcgtctt ggttcaactc cttcctaaca    2160
catgcattaa gatagttgtg gcaatgctac tatttgctat ccatactgtc caaaaaagta    2220
ccttgtttct act                                                       2233
```

<210> SEQ ID NO 4
<211> LENGTH: 1773
<212> TYPE: DNA
<213> ORGANISM: Influenza virus A/Singapore/1/57/ca

<400> SEQUENCE: 4

```
agcaaaagca ggggttatac catagacaac cagaagcaaa acaatggcca tcatttatct      60
cattctcctg ttcacagcag tgagagggga ccagatatgc attggatacc atgccaataa     120
ttccacagag aaggtcgaca caattctaga gcagaacgtc actgtgactc atgccaagga     180
cattcttgag aagacccata cggaaagtt atgcaaacta acggaatcc ctccacttga      240 actagggggac tgtagcattg ccggatggct ccttggaaat ccagaatgtg ataggcttct     300
aagtgtgcca gaatggtcct atataatgga gaagaaaac ccgagagacg gtttgtgtta      360
tccaggcagc ttcaatgatt atgaagaatt gaaacatctc ctcagcagcg tgaaacattt     420
cgagaaagta aagattctgc ccaaagatag atggacacag catacaacaa ctggaggttc     480
acgggcctgc gcggtgtctg gtaatccatc attcttcagg aacatggtct ggctgacaaa     540
gaaagaatca aattatccgg ttgccaaagg atcgtacaac aatacaagcg agaacaaat      600 gctaataatt tgggggggtgc accatcccaa tgatgagaca gaacaaagaa cattgtacca     660
gaatgtggga acctatgttt ccgtaggcac atcaacattg aacaaaggt caaccccaga      720 catagcaaca aggcctaaag tgaatggact aggaagtaga atggaattct cttggaccct     780
attggatatg tgggacacca taaattttga gagtactggt aatctaattg caccagagta     840
tggattcaaa atatcgaaaa gaggtaattc agggatcatg aaaacagaag gaacacttga     900
gaactgtgag accaaatgcc aaactccttt gggagcaata aatacaacat gccttttca      960 caatgtccac ccactgacaa taggtgagtg ccccaaatat gtaaaatcgg agaagttggt     1020
cttagcaaca ggaccaagga atgttcccca gattgaatca gagaggattgt ttggggcaat    1080 agctgggttt atagaagag gatggcaagg aatggttgat ggttggtatg gataccatca     1140
cagcaatgac cagggatcag gtatgcagc agacaaagaa tccactcaaa aggcatttga     1200
tggaatcacc aacaaggtaa attctgtgat tgaaagatg aacacccaat ttgaagctgt     1260
tgggaaagaa ttcagtaact tagagagaag actggagaac ttgaacaaaa agatggaaga     1320
cgggtttcta gatgtgtgga catacaatgc tgagcttcta gttctgatgg aaaatgagag     1380
gacacttgac tttcatgatt ctaatgtcaa gaatctgtat gataaagtca gaatgcagct     1440
gagagacaac gtcaaagaac taggaaatgg atgttttgaa ttttatcaca aatgtgatga     1500
tgaatgcatg aatagtgtga aaacgggac gtatgattat cccaagtatg aagaagagtc     1560
taaactaaat agaaatgaaa tcaaggggggt aaaattgagc agcatggggg tttatcaaat     1620
ccttgccatt tatgctacag tagcaggttc tctgtcactg gcaatcatga tggctgggat     1680
ctctttctgg atgtgctcca acgggtctct gcagtgcagg atctgcatat gattataagt     1740
cattttataa ttaaaaacac ccttgtttct act                                 1773
```

<210> SEQ ID NO 5
<211> LENGTH: 1565
<212> TYPE: DNA
<213> ORGANISM: Influenza virus A/Singapore/1/57/ca

<400> SEQUENCE: 5

```
agcaaaagca gggtagataa tcactcactg agtgacatca aaatcatggc gtcccaaggc      60
accaaacggt cttatgaaca gatggaaact gatggggaac gccagaatgc aactgaaatc     120
agagcatccg tcgggaagat gattgatgga attggacgat tctacatcca aatgtgcacc     180
gaacttaaac tcagtgatta tgaggggcga ctgatccaga acagcttaac aatagagaga     240
atggtgctct ctgcttttga cgagaggagg aataaatatc tggaagaaca tcccagcgcg     300
gggaaggatc ctaagaaaac tggaggaccc atatacaaga gagtaaatgg aaagtggatg     360
agggaactcg tcctttatga caaagaagaa ataaggcgaa tctggcgcca agctaataat     420
ggtgatgatg caacagctgg tctgactcac atgatgatct ggcattccaa tttgaatgat     480
acaacatacc agaggacaag agctcttgtt cgcaccggaa tggatccag atgtgctct     540
ttgatgcagg gttcgactct ccctaggagg tctggagccg caggcgctgc agtcaaagga     600
gttgggacaa tggtgatgga gttgatcagg atgatcaaac gtgggatcaa tgatcggaac     660
ttctggagag gtgagaatgg gcggaaaaca aggattgctt atgagagaat gtgcaacatt     720
ctcaaaggaa aatttcaaac agctgcacaa agagcaatga tggatcaagt gagagaaagc     780
cggaacccag aaatgctga gatcgaagat ctcatctttc tggcacggtc tgcactcata     840
ttgagagggt cagttgctca caaatcttgt ctgcctgcct gtgtgtatgg aactgccgta     900
gccagtgggt acgacttcga aaagagggga tactctttag tagggataga ccctttcaaa     960
ctgcttcaaa acagccaagt atacagccta atcagaccga acgagaatcc agcacacaag    1020
agtcagctgg tgtggatggc atgcaattct gctgcatttg aagatctaag agtatcaagc    1080
ttcatcagag ggaccaaagt aatcccaagg gggaaacttt ccactagagg agtacaaatt    1140
gcttcaaatg aaaacatgga tactatggaa tcaagtactc ttgaactgag aagcaggtac    1200
tgggccataa ggaccagaag tggaggaaac actaatcaac agagggcctc tgcaggtcaa    1260
atcagtgtac aacctacgtt ttctgtgcaa agaaacctcc catttgacaa aacaaccatc    1320
atggcagcat tcactgggaa tgcagaggga agaacatcag acatgagggc agaaatcata    1380
aggatgatgg aaggtgcaaa accagaagaa gtgtccttcc aggggcgggg agtcttcgag    1440
ctctcggacg aaaaggcaac gaacccgatc gtgccctctt ttgacatgag taatgaagga    1500
tcttatttct tcggagacaa tgcagaggag tacgacaatt aaggaaaaat accttgtttc    1560
tact                                                                 1565
```

<210> SEQ ID NO 6
<211> LENGTH: 1466
<212> TYPE: DNA
<213> ORGANISM: Influenza virus A/Singapore/1/57/ca

<400> SEQUENCE: 6

```
agcaaaagca ggagtgaaga tgaatccaaa tcaaaagata ataacaattg gctctgtctc      60
tctcaccatt gcaacagtat gcttcctcat gcagattgcc atcctggcaa ctactgtgac     120
attgcatttt aaacaacatg agtgcgactc ccccgcgagc aaccaagtaa tgccatgtga     180
accaataata atagaaagga acataacaga gatagtgtat ttgaataaca ccaccataga     240
gaaagagatt tgccccgaag tagtggaata cagaaattgg tcaaagccgc aatgtcaaat     300
tacaggattt gcacctttt ctaaggacaa ttcaatccgg ctttctgctg gtggggacat     360
ttgggtgacg agagaacctt atgtgtcatg cgatcctggc aagtgttatc aatttgcact     420
```

```
cgggcagggg accacactat acaacaaaca ttcaaatggc acaatacatg atagaatccc      480
tcatcgaacc ctattaatga atgagttggg tgttccattt catttaggaa ccaaacaagt      540
gtgtgtagca tggtccagct caagttgtca cgatggaaaa gcatggttgc atgtttgtgt      600
cactggggat gatagaaatg cgactgctag cttcatttat gacgggaggc ttgtggacag      660
tattggttca tggtctcaaa atatcctcag gacccaggag tcggaatgcg tttgtatcaa      720
tgggacttgc acagtagtaa tgactgatgg aagtgcatca ggaagagccg atactagaat      780
actattcatt aaagagggga aaattgtccg tattagccca ttgtcaggaa gtgctcagca      840
tatagaggag tgttcctgtt accctcgata tcctgacgtc agatgtatct gcagagacaa      900
ctggaaaggc tctaataggc ccgttataga cataaatatg aagattata gcattgattc      960
cagttatgtg tgctcaggc ttgttggcga cacacccagg aacgacgaca gctctagcaa     1020
tagcaattgc agggatccta acaatgagag agggaatcca ggagtgaaag gctgggcctt     1080
tgacaatgga gatgatgtat ggatgggaag aacaatcaac aaagattcac gctcaggtta     1140
tgaaactttc aaagtcattg gtggttggtc cacacctaat tccaaatcgc aggtcaatag     1200
acaggtcata gttgacaaca ataattggtc tggttactct ggtatttct ctgttgaggg     1260
caaaagctgc atcaataggt gcttttatgt ggagttgata aggggaaggc cacaggagac     1320
tagagtatgg tggaccctcaa acagtattgt tgtgttttgt ggcacttcag gtacttatgg     1380
aacaggctca tggcctgatg gggcgaacat caatttcatg cctatataag ctttcgcaat     1440
tttagaaaaa actccttgtt tctact                                           1466

<210> SEQ ID NO 7
<211> LENGTH: 1027
<212> TYPE: DNA
<213> ORGANISM: Influenza virus A/Singapore/1/57/ca

<400> SEQUENCE: 7
agcaaaagca ggtagatatt gaaagatgag tcttctaacc gaggtcgaaa cgtatgttct       60
ctctatcgtc ccgtcaggcc ccctcaaagc cgagatcgca cagagacttg aagatgtctt      120
tgctgggaag aacaccgatc ttgaggctct catggaatgg ctaaagacaa gaccaatcct      180
gtcacctctg actaagggga ttttgggatt tgtattcacg ctcaccgtgc ccagtgagcg      240
aggactgcag cgtagacgct ttgtccaaaa tgcccctcaat gggaatgggg atccaaataa      300
catggacaga gcagttaaac tgtataaaaa gcttaagagg gagataacat tccatggggc      360
caaagaaata gcgctcagtt attctgctgg tgcacttgcc agttgtatgg gcctcatata      420
caacaggatg ggggctgtga ccactgaagt ggccttttggc ctggtatgtg caacctgtga      480
acagattgct gactcccacc ataggtctca taggcaaatg gtgacaacaa ccaatccact      540
aataagacat gagaacagaa tggttctggc cagcactaca gctaaggcta tggagcaaat      600
ggctggatcg agtgagcaag cagcagaggc catggaggtt gctagtcagg ccaggcaaat      660
ggtgcaggca atgagagcca ttgggactca tcctagctcc agtgctggtc taaaagatga      720
tcttcttgaa aatttgcagg cctatcagaa acgaatgggg gtgcagatgc aacgattcaa      780
gtgacccctct tgttgttgcc gcgagtatca ttgggatctt gcacttgata ttgtggattc      840
ttgatcgtct ttttttcaaa tgcatttatc gcttctttaa acacggtctg aaaagagggc      900
cttctacgga aggagtacca gagtctatga gggaagaata tcgaaggaa cagcagagtg      960
ctgtggatgc tgacgatagt cattttgtca gcatagagct ggagtaaaaa actaccttgt     1020
ttctact                                                               1027
```

<210> SEQ ID NO 8
<211> LENGTH: 890
<212> TYPE: DNA
<213> ORGANISM: Influenza virus A/Singapore/1/57/ca

<400> SEQUENCE: 8

```
agcaaaagca gggtgacaaa gacataatgg atcctaacac tgtgtcaagc tttcaggtag     60
attgcttcct ttggcatgtc cgcaaacaag ttgcagacca agaactaggt gatgccccat    120
tccttgatcg gcttcgccga gatcagaagt ccctaagggg aagaggcagc actctcggtc    180
tgaacatcga aacagccacc cgtgttggaa agcagatagt ggagaggatt ctgaaggaag    240
aatccgatga ggcacttaaa atgaccatgg cctccgcacc tgcttcgcga tacctaactg    300
acatgactat tgaggaaatg tcaagggact ggttcatgct aatgcccaag cagaaagtgt    360
caggccctct ttgtatcaga atggaccagg caatcatgga taagaacatc atattgaaag    420
cgaatttcag tgtgattttt gaccggctag agaccctaat attactaagg gctttcaccg    480
aagagggagc aattgttggc gaaatttcac cattgccttc tcttccagga catactaatg    540
aggatgtcaa aaatgcaatt ggggtcctca tcggaggact tgaatggaat gataacacag    600
ttcgagtctc taaaactcta cagagattcg cttggagaaa cagtaatgag aatgggagac    660
ctccactcac tccaaaacag aaacggaaaa tggcgagaac aattaggtca aaagttcgaa    720
gaaataagat ggctgattga agaagtgaga cacaaattga agataacaga gaatagtttt    780
gagcaaataa catttatgca agccttacag ctgctatttg aagtggaaca agagataaga    840
actttctcgt ttcagcttat ttaatgataa aaaacaccct tgtttctact               890
```

<210> SEQ ID NO 9
<211> LENGTH: 771
<212> TYPE: PRT
<213> ORGANISM: Influenza virus A/Singapore/1/57/ca
<220> FEATURE:
<221> NAME/KEY: MISC_FEATURE
<222> LOCATION: (760)..(760)
<223> OTHER INFORMATION: Any amino acid
<220> FEATURE:
<221> NAME/KEY: MISC_FEATURE
<222> LOCATION: (762)..(762)
<223> OTHER INFORMATION: Any amino acid
<220> FEATURE:
<221> NAME/KEY: MISC_FEATURE
<222> LOCATION: (765)..(765)
<223> OTHER INFORMATION: Any amino acid

<400> SEQUENCE: 9

```
Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Met Thr Ser Thr Val His Tyr Pro
            100                 105                 110
```

-continued

```
Lys Ile Tyr Lys Thr Tyr Phe Glu Lys Val Glu Arg Leu Lys His Gly
            115                 120                 125
Thr Phe Gly Pro Val His Phe Arg Asn Gln Val Lys Ile Arg Arg Arg
        130                 135                 140
Val Asp Ile Asn Pro Gly His Ala Asp Leu Ser Ala Lys Glu Ala Gln
145                 150                 155                 160
Asp Val Ile Met Glu Val Val Phe Pro Asn Glu Val Gly Ala Arg Ile
                165                 170                 175
Leu Thr Ser Glu Ser Gln Leu Thr Thr Thr Lys Glu Lys Lys Glu Glu
            180                 185                 190
Leu Gln Asp Cys Lys Ile Ser Pro Leu Met Val Ala Tyr Met Leu Glu
        195                 200                 205
Arg Glu Leu Val Arg Lys Thr Arg Phe Leu Pro Val Ala Gly Gly Thr
    210                 215                 220
Ser Ser Val Tyr Ile Glu Val Leu His Leu Thr Gln Gly Thr Cys Trp
225                 230                 235                 240
Glu Gln Met Tyr Thr Pro Gly Gly Glu Val Arg Asn Asp Asp Val Asp
                245                 250                 255
Gln Ser Leu Ile Ile Ala Ala Arg Asn Ile Val Arg Arg Ala Ala Val
            260                 265                 270
Ser Ala Asp Pro Leu Ala Ser Leu Leu Glu Met Cys His Ser Thr Gln
        275                 280                 285
Ile Gly Gly Thr Arg Met Val Asp Ile Leu Arg Gln Asn Pro Thr Glu
    290                 295                 300
Glu Gln Ala Val Asp Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Ile Glu Glu Val Leu Thr Gly Asn Leu Gln Thr Leu
            340                 345                 350
Lys Ile Arg Val His Glu Gly Tyr Glu Glu Phe Thr Met Val Gly Lys
        355                 360                 365
Arg Ala Thr Ala Ile Leu Arg Lys Ala Thr Arg Leu Ile Gln Leu
    370                 375                 380
Ile Val Ser Gly Arg Asp Glu Gln Ser Ile Ala Glu Ala Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
        435                 440                 445
Trp Gly Ile Glu His Ile Asp Asn Val Met Gly Met Ile Gly Val Leu
    450                 455                 460
Pro Asp Met Thr Pro Ser Thr Glu Met Ser Met Arg Gly Val Arg Val
465                 470                 475                 480
Ser Lys Met Gly Val Asp Glu Tyr Ser Ser Ala Glu Arg Val Val Val
                485                 490                 495
Ser Ile Asp Arg Phe Leu Arg Val Arg Asp Gln Arg Gly Asn Val Leu
            500                 505                 510
Leu Ser Pro Glu Glu Val Ser Glu Thr Gln Gly Thr Glu Lys Leu Thr
        515                 520                 525
```

```
Ile Thr Tyr Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Ile Leu Gly Lys Asp Ala
            660                 665                 670

Gly Thr Leu Thr Glu Asp Pro Asp Glu Gly Thr Ser Gly Val Glu Ser
        675                 680                 685

Ala Val Leu Arg Gly Phe Leu Ile Leu Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn Xaa Cys Xaa Ile Val Xaa Lys Arg Pro
        755                 760                 765

Cys Phe Tyr
        770

<210> SEQ ID NO 10
<211> LENGTH: 757
<212> TYPE: PRT
<213> ORGANISM: Influenza virus A/Singapore/1/57/ca

<400> SEQUENCE: 10

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125
```

-continued

```
Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Ile Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Val Ser Leu Ser Pro Gly Met Met Met Gly Met Phe Asn Met Leu Ser
                405                 410                 415

Thr Val Ile Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540
```

```
Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
                580                 585                 590

Asp Gly Gly Pro Asn Leu Tyr Asn Ile Arg Asn Leu His Ile Pro Glu
                595                 600                 605

Val Cys Leu Lys Trp Glu Leu Met Asp Glu Asp Tyr Gln Gly Arg Leu
            610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
                740                 745                 750

Leu Arg Arg Gln Lys
            755

<210> SEQ ID NO 11
<211> LENGTH: 716
<212> TYPE: PRT
<213> ORGANISM: Influenza virus A/Singapore/1/57/ca

<400> SEQUENCE: 11

Met Glu Asp Phe Val Arg Gln Cys Phe Asn Pro Met Ile Val Glu Leu
1               5                   10                  15

Ala Glu Arg Ala Met Lys Glu Tyr Gly Glu Asp Leu Lys Ile Glu Thr
                20                  25                  30

Asn Lys Phe Ala Ala Ile Cys Thr His Leu Glu Val Cys Phe Met Tyr
            35                  40                  45

Ser Asp Phe His Phe Ile Asn Glu Gln Gly Glu Ser Ile Ile Val Glu
        50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160
```

-continued

```
Tyr Thr Leu Asp Glu Glu Ser Arg Ala Arg Ile Lys Thr Arg Leu Phe
            165                 170                 175

Thr Ile Arg Gln Glu Met Ala Ser Arg Gly Leu Trp Asp Ser Phe Arg
        180                 185                 190

Gln Ser Glu Arg Gly Glu Thr Ile Glu Glu Arg Phe Glu Ile Thr
    195                 200                 205

Gly Thr Met Arg Arg Leu Ala Asp Gln Ser Leu Pro Pro Asn Phe Ser
210                 215                 220

Cys Leu Glu Ile Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Lys
                245                 250                 255

Ile Glu Pro Phe Leu Lys Thr Thr Pro Arg Pro Ile Arg Leu Pro Asp
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Tyr Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Arg Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Arg Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asn Ser Ile Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Val Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575
```

```
Trp Gly Met Glu Met Arg Arg Cys Leu Leu Gln Ser Leu Gln Gln Ile
            580                 585                 590

Glu Ser Met Ile Glu Ala Gln Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
                660                 665                 670

Arg Asp Asn Leu Glu Pro Gly Thr Phe Asp Leu Gly Gly Leu Tyr Glu
                675                 680                 685

Ala Ile Glu Glu Cys Leu Ile Asn Asp Pro Trp Val Leu Leu Asn Ala
                690                 695                 700

Ser Trp Phe Asn Ser Phe Leu Thr His Ala Leu Arg
705                 710                 715

<210> SEQ ID NO 12
<211> LENGTH: 562
<212> TYPE: PRT
<213> ORGANISM: Influenza virus A/Singapore/1/57/ca

<400> SEQUENCE: 12

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Gln Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Glu Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Leu Gly Ser Arg Met
225                 230                 235                 240
```

-continued

```
Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Asn Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Pro Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile

<210> SEQ ID NO 13
<211> LENGTH: 506
<212> TYPE: PRT
<213> ORGANISM: Influenza virus A/Singapore/1/57/ca
<220> FEATURE:
<221> NAME/KEY: MISC_FEATURE
<222> LOCATION: (499)..(499)
<223> OTHER INFORMATION: Any amino acid

<400> SEQUENCE: 13

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
```

```
                20                  25                  30
Ile Asp Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
        50                  55                  60

Arg Met Val Leu Ser Ala Phe Asp Glu Arg Asn Lys Tyr Leu Glu
65                  70                  75                  80

Glu His Pro Ser Ala Gly Lys Asp Pro Lys Thr Gly Gly Pro Ile
                85                  90                  95

Tyr Lys Arg Val Asn Gly Lys Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Thr Ala Val Ala Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Ser Ser Phe Ile Arg Gly Thr Lys Val
            340                 345                 350

Ile Pro Arg Gly Lys Leu Ser Thr Arg Gly Val Gln Ile Ala Ser Asn
        355                 360                 365

Glu Asn Met Asp Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Asp Lys Thr Thr Ile Met Ala Ala Phe Thr Gly Asn
            420                 425                 430

Ala Glu Gly Arg Thr Ser Asp Met Arg Ala Glu Ile Ile Arg Met Met
        435                 440                 445
```

```
Glu Gly Ala Lys Pro Glu Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn Xaa Gly Lys Ile Pro Leu Phe Leu
            500                 505

<210> SEQ ID NO 14
<211> LENGTH: 469
<212> TYPE: PRT
<213> ORGANISM: Influenza virus A/Singapore/1/57/ca

<400> SEQUENCE: 14

Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Ala Thr Thr
                20                  25                  30

Val Thr Leu His Phe Lys Gln His Glu Cys Asp Ser Pro Ala Ser Asn
            35                  40                  45

Gln Val Met Pro Cys Glu Pro Ile Ile Ile Glu Arg Asn Ile Thr Glu
        50                  55                  60

Ile Val Tyr Leu Asn Asn Thr Thr Ile Glu Lys Glu Ile Cys Pro Glu
65                  70                  75                  80

Val Val Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Gly Lys
        115                 120                 125

Cys Tyr Gln Phe Ala Leu Gly Gln Gly Thr Thr Leu Tyr Asn Lys His
130                 135                 140

Ser Asn Gly Thr Ile His Asp Arg Ile Pro His Arg Thr Leu Leu Met
145                 150                 155                 160

Asn Glu Leu Gly Val Pro Phe His Leu Gly Thr Lys Gln Val Cys Val
                165                 170                 175

Ala Trp Ser Ser Ser Cys His Asp Gly Lys Ala Trp Leu His Val
            180                 185                 190

Cys Val Thr Gly Asp Asp Arg Asn Ala Thr Ala Ser Phe Ile Tyr Asp
        195                 200                 205

Gly Arg Leu Val Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Lys Glu Gly Lys Ile Val Arg Ile Ser Pro Leu Ser Gly Ser Ala
            260                 265                 270

Gln His Ile Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Val Ile Asp
    290                 295                 300

Ile Asn Met Glu Asp Tyr Ser Ile Asp Ser Ser Tyr Val Cys Ser Gly
```

-continued

```
            305                 310                 315                 320
Leu Val Gly Asp Thr Pro Arg Asn Asp Asp Ser Ser Asn Ser Asn
                325                 330                 335

Cys Arg Asp Pro Asn Asn Glu Arg Gly Asn Pro Gly Val Lys Gly Trp
                340                 345                 350

Ala Phe Asp Asn Gly Asp Asp Val Trp Met Gly Arg Thr Ile Asn Lys
                355                 360                 365

Asp Ser Arg Ser Gly Tyr Glu Thr Phe Lys Val Ile Gly Gly Trp Ser
    370                 375                 380

Thr Pro Asn Ser Lys Ser Gln Val Asn Arg Gln Val Ile Val Asp Asn
385                 390                 395                 400

Asn Asn Trp Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Pro Gln
                420                 425                 430

Glu Thr Arg Val Trp Trp Thr Ser Asn Ser Ile Val Val Phe Cys Gly
                435                 440                 445

Thr Ser Gly Thr Tyr Gly Thr Gly Ser Trp Pro Asp Gly Ala Asn Ile
                450                 455                 460

Asn Phe Met Pro Ile
465

<210> SEQ ID NO 15
<211> LENGTH: 252
<212> TYPE: PRT
<213> ORGANISM: Influenza virus A/Singapore/1/57/ca

<400> SEQUENCE: 15

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
                100                 105                 110

Lys Glu Ile Ala Leu Ser Tyr Ser Ala Gly Ala Leu Ala Ser Cys Met
            115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser His His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
                180                 185                 190

Ala Gly Ser Ser Glu Gln Ala Ala Glu Ala Met Glu Val Ala Ser Gln
            195                 200                 205
```

-continued

```
Ala Arg Gln Met Val Gln Ala Met Arg Ala Ile Gly Thr His Pro Ser
    210                 215                 220
Ser Ser Ala Gly Leu Lys Asp Asp Leu Leu Glu Asn Leu Gln Ala Tyr
225                 230                 235                 240
Gln Lys Arg Met Gly Val Gln Met Gln Arg Phe Lys
                245                 250

<210> SEQ ID NO 16
<211> LENGTH: 97
<212> TYPE: PRT
<213> ORGANISM: Influenza virus A/Singapore/1/57/ca

<400> SEQUENCE: 16

Met Ser Leu Leu Thr Glu Val Glu Thr Pro Ile Arg Asn Glu Trp Gly
1               5                   10                  15
Cys Arg Cys Asn Asp Ser Ser Asp Pro Leu Val Val Ala Ala Ser Ile
                20                  25                  30
Ile Gly Ile Leu His Leu Ile Leu Trp Ile Leu Asp Arg Leu Phe Phe
            35                  40                  45
Lys Cys Ile Tyr Arg Phe Phe Lys His Gly Leu Lys Arg Gly Pro Ser
        50                  55                  60
Thr Glu Gly Val Pro Glu Ser Met Arg Glu Glu Tyr Arg Lys Glu Gln
65                  70                  75                  80
Gln Ser Ala Val Asp Ala Asp Asp Ser His Phe Val Ser Ile Glu Leu
                85                  90                  95
Glu

<210> SEQ ID NO 17
<211> LENGTH: 237
<212> TYPE: PRT
<213> ORGANISM: Influenza virus A/Singapore/1/57/ca

<400> SEQUENCE: 17

Met Asp Pro Asn Thr Val Ser Ser Phe Gln Val Asp Cys Phe Leu Trp
1               5                   10                  15
His Val Arg Lys Gln Val Ala Asp Gln Glu Leu Gly Asp Ala Pro Phe
                20                  25                  30
Leu Asp Arg Leu Arg Arg Asp Gln Lys Ser Leu Arg Gly Arg Gly Ser
            35                  40                  45
Thr Leu Gly Leu Asn Ile Glu Thr Ala Thr Arg Val Gly Lys Gln Ile
        50                  55                  60
Val Glu Arg Ile Leu Lys Glu Glu Ser Asp Glu Ala Leu Lys Met Thr
65                  70                  75                  80
Met Ala Ser Ala Pro Ala Ser Arg Tyr Leu Thr Asp Met Thr Ile Glu
                85                  90                  95
Glu Met Ser Arg Asp Trp Phe Met Leu Met Pro Lys Gln Lys Val Ser
                100                 105                 110
Gly Pro Leu Cys Ile Arg Met Asp Gln Ala Ile Met Asp Lys Asn Ile
            115                 120                 125
Ile Leu Lys Ala Asn Phe Ser Val Ile Phe Asp Arg Leu Glu Thr Leu
        130                 135                 140
Ile Leu Leu Arg Ala Phe Thr Glu Glu Gly Ala Ile Val Gly Glu Ile
145                 150                 155                 160
Ser Pro Leu Pro Ser Leu Pro Gly His Thr Asn Glu Asp Val Lys Asn
                165                 170                 175
Ala Ile Gly Val Leu Ile Gly Gly Leu Glu Trp Asn Asp Asn Thr Val
```

-continued

```
              180            185              190
Arg Val Ser Lys Thr Leu Gln Arg Phe Ala Trp Arg Asn Ser Asn Glu
        195                 200                 205
Asn Gly Arg Pro Pro Leu Thr Pro Lys Gln Lys Arg Lys Met Ala Arg
    210                 215                 220
Thr Ile Arg Ser Lys Val Arg Arg Asn Lys Met Ala Asp
225                 230                 235
```

<210> SEQ ID NO 18
<211> LENGTH: 121
<212> TYPE: PRT
<213> ORGANISM: Influenza virus A/Singapore/1/57/ca

<400> SEQUENCE: 18

```
Met Asp Pro Asn Thr Val Ser Ser Phe Gln Asp Ile Leu Met Arg Met
1               5                   10                  15
Ser Lys Met Gln Leu Gly Ser Ser Glu Asp Leu Asn Gly Met Ile
            20                  25                  30
Thr Gln Phe Glu Ser Leu Lys Leu Tyr Arg Asp Ser Leu Gly Glu Thr
        35                  40                  45
Val Met Arg Met Gly Asp Leu His Ser Leu Gln Asn Arg Asn Gly Lys
    50                  55                  60
Trp Arg Glu Gln Leu Gly Gln Lys Phe Glu Glu Ile Arg Trp Leu Ile
65                  70                  75                  80
Glu Glu Val Arg His Lys Leu Lys Ile Thr Glu Asn Ser Phe Glu Gln
                85                  90                  95
Ile Thr Phe Met Gln Ala Leu Gln Leu Leu Phe Glu Val Glu Gln Glu
                100                 105                 110
Ile Arg Thr Phe Ser Phe Gln Leu Ile
            115                 120
```

<210> SEQ ID NO 19
<211> LENGTH: 2396
<212> TYPE: DNA
<213> ORGANISM: Influenza B/Vienna/1/99/ca

<400> SEQUENCE: 19

```
agcagaagcg agcgttttc aagatgacat tggctaaaat tgaattgtta aaacaactgt      60
taagggacaa tgaagccaaa acagtattga acaaacaac agtagatcaa tataacataa     120
taagaaaatt caatacatca agaattgaaa agaacccttc attaaggatg aagtgggcaa     180
tgtgttctaa ttttcccttg ctttgaccaa gggtgacat ggcaaacaga atccccttgg     240
aatcaagggg aatacaactt aaaacaaatg ctgaagacat aggaaccaaa ggccaaatgt     300
gctcaatagc agcagttacc tggtggaata catatggacc aataggagat actgaaggtt     360
tcgaaaaagt ctacgaaagc ttttttctca gaaagatgag acttgacaat gcccacttggg    420
gccgaataac ttttggccca gttgaaagag taagaaaaag ggtactgcta aaccctctca     480
ccaaggaaat gcctccagat gaagcaagta atgtgataat ggaaatattg ttccctaagg     540
aagcaggaat accaagagaa tctacttgga cataggga actgataaaa gaaaaaagag      600
aaaaattgaa ggaacgatg ataactccca ttgtactggc atacatgctt gagagggaat     660
tggttgccag agaaggttc ctgccggtag caggagcaac atcagctgag ttcatagaaa     720
tgctacactg cttacaaggt gaaaattgga gacaaatata tcacccggga gggaataaac     780
taactgaatc taggtctcaa tcgatgattg tggcttgtag aaagataatc agaagatcaa     840
```

```
tagtcgcatc aaacccattg gagctagctg tagaaattgc aaacaagact gtaatagata    900
ctgaaccttt aaaatcatgt ctgacagcca tagacggagg tgatgtcgcc tgtgacataa    960
taagggctgc attaggacta aagatcagac aaagacaaag atttggacga cttgaactaa   1020
agagaatatc aggaagagga ttcaaaaatg atgaagaaat attaatcggg aacggaacaa   1080
tacagaagat tggaatatgg gacggagaag aggagttcca tgtaagatgt ggtgaatgca   1140
ggggaatatt aaaaaagagc aaaatgagaa tggaaaaact actaataaat tcagctaaaa   1200
aggaagacat gaaagattta ataatcttgt gcatggtatt ttctcaagac actaggatgt   1260
tccaaggagt gaggggagaa ataaattttc ttaatagaag gccaacttt ttatctccaa   1320
tgtatcaact ccaaagatat ttttgaata gaagtaatga tctctttgat caatggggt    1380
atgaggaatc acccaaagca agtgagctac atgggataaa tgaattaatg aatgcatctg   1440
actacacttt gaaagggtt gtagtaacaa aaatgtgat tgatgatttt agttctactg    1500
aaacagaaaa agtatctata acaaaaaatc ttagtttaat aaaaaggact ggggaagtca   1560
taatgggagc caatgacgta agtgaattag aatcacaagc tcagctaatg ataacatatg   1620
atacacctaa gatgtgggag atgggaacaa ccaaagaact ggtgcaaaac acctatcaat   1680
gggtgctgaa aaatttggta acactgaagg ctcagtttct tctaggaaaa gaagacatgt   1740
tccaatggga tgcatttgaa gcatttgaaa gcataatccc ccagaagatg gctggccaat   1800
acagtggatt tgcaagagca gtgctcaaac aaatgagaga ccaagaggtc atgaaaactg   1860
accagttcat aaagttgttg cccttttgtt tctcaccacc aaagttaagg agcaatgggg   1920
agccttatca gttcttgagg cttgtattga agggaggagg agaaaatttc atcgaagtaa   1980
ggaaagggtc tcctctattc tcttacaatc cacaaacaga agtcctaact atatgcggca   2040
gaatgatgtc attaaaaggg aaaattgaag atgaagaaag gaatagatca atggggaatg   2100
cagtgttggc gggttttctt gttagtggca agtatgaccc agatcttgga gatttcaaaa   2160
ctattgaaga gcttgaaaag ctaaaaccgg gggagaaagc aaacatctta ctttatcaag   2220
gaaagcccgt taagtagtt aaaaggaaaa gatatagtgc tttatccaat gacatttcac    2280
aaggaattaa gagacaaaga atgacagttg agtccatggg gtgggccttg agctaatata   2340
aatttatcca ttaattcaat gaatgcaatt gagtgaaaaa tgctcgtgtt tctcat        2396
```

<210> SEQ ID NO 20
<211> LENGTH: 2369
<212> TYPE: DNA
<213> ORGANISM: Influenza B/Vienna/1/99/ca

<400> SEQUENCE: 20

```
agcagaagcg gagccttaa gatgaatata atccttatt ttctcttcat agatgtaccc     60
atacaggcag caatttcaac aacattccca tacaccggtg ttccccctta ttcccatgga   120
acggaacag gccacacaat agacaccgtg atcgaacac atgagtactc gaacaaagga    180
aaacagtatg tttctgacat cacaggatgt acaatggtag atccaacaaa tggaccatta   240
cccgaagaca atgagccaag tgcctatgca caattagatt gcgttctgga ggctttggat   300
agaatggatg aggaacatcc aggtctgttt caagcagcct cacagaatgc catggaggca   360
ctaatggtca caactgtaga caattaacc caggggagac agactttcga ttggacagta   420
tgcagaaatc agcctgctgc aacggcacta acacaacaa taacctcctt taggttgaat   480
gatttgaatg gagctgacaa gggtggattg gtacccttt gccaagatat cattgattca   540
ttagacaagc ctgaaatgac tttcttctca gtaaagaata taaagaaaaa attccctgct   600
```

```
aaaaacagaa agggtttcct cataaagaga ataccaatga aagtaaaaga caggatatcc    660
agagtggaat acatcaaaag agcattgtca ttaaacacaa tgacaaaaga tgctgaaagg    720
ggcaaactaa aaagaagagc gattgcaacc gctggaatac aaatcagagg gtttgtatta    780
gtagttgaaa acttggctaa aaatatctgt gaaaatctag aacaaagtgg tttgcccgta    840
ggtggaaatg aaaagaaggc caaactgtca aatgcagtgg ccaaaatgct cagtaactgc    900
ccaccaggag ggatcagcat gacagtaaca ggagacaata ctaaatggaa tgaatgctta    960
aatccaagag tcttttttgc tatgactgaa agaataacca gagacagccc aatttggttc   1020
cgggattttt gtagtatagc accggtcttg ttctccaata aaatagccag attgggaaaa   1080
ggatttatga taacaagtaa aacaaaaaga ctgaaggctc aaataccttg tcctgatctg   1140
tttagcatac cattagaaag atataatgaa gaaacaaggg caaaattaaa aaagctgaaa   1200
ccattcttca atgaagaagg aacggcatct ttgtcgcctg aatgatgat gggaatgttt   1260 aatatgctat ctaccgtgtt gggagtagca gcactaggta tcaaaaacat tggaaacaag   1320
gaatacttat gggatggact gcaatcttct gatgattttg ctctgtttgt taatgcaaaa   1380
gatgaagaga catgtatgga aggaataaac gattttacc gaacatgtaa attattggga   1440
ataaacatga gcaaaagaa aagttactgt aacgaaactg gaatgtttga atttacaagc   1500
atgttctata gagatggatt tgtatctaac tttgcaatgg aaattccttc atttggagtt   1560
gctggagtaa atgaatcagc agatatggca ataggaatga caataataaa gaacaatatg   1620
attaacaatg ggatgggtcc agcaacagca caaacagcca tacaattgtt catagctgat   1680
tataggtaca cctacaaatg ccacagagga gattccaaag tggaaggaaa agaatgaaa   1740 attataaagg agctatggga aaacactaaa ggaagagatg gtctgttagt ggcagatggt   1800
gggcccaaca tttacaattt gagaaactta catatcccag aaatagtatt gaagtacaat   1860
ctaatggacc ctgaatacaa agggcggtta cttcaccctc aaaatccctt tgtaggacat   1920
ttgtctattg aaggcatcaa agaagcagat ataaccccag cacatggtcc tgtgaagaaa   1980
atggattatg atgcagtgtc tggaactcat agttggagaa ccaaaaggaa cagatctata   2040
ctaaatactg atcagaggaa catgattctt gaggaacaat gctacgctaa atgttgcaac   2100 cttttttgagg cctgttttaa cagtgcatca tacaggaaac cagtagggca gcacagcatg   2160
cttgaggcta tggcccatag attaagaatg gatgcacgac tggattatga atcaggaaga   2220
atgtcaaagg atgattttga gaagcaatg gctcaccttg gtgagattgg gtacacataa   2280
gctccgaaga tgtccatggg gttattggtc atcattggat acatgtgata aacaaatgat   2340
taaaatgaaa aaaggctcgt gtttctact                                    2369

<210> SEQ ID NO 21
<211> LENGTH: 2305
<212> TYPE: DNA
<213> ORGANISM: Influenza B/Vienna/1/99/ca

<400> SEQUENCE: 21
agcagaagcg gtgcgtttga tttgtcataa tggatacttt tattacaaga aacttccaga     60
ctacaataat acaaaaggcc aaaaacacaa tggcagaatt tagtgaagat cctgaattac    120
aaccagcaat gctattcaac atctgcgtcc atctagaggt ttgctatgta ataagtgaca    180 tgaatttct tgacgaagaa ggaaaagcat atacagcatt agaaggacaa gggaaagaac    240
aaaatttgag accacaatat gaagtaattg agggaatgcc aagaaccata gcatggatgg    300
```

-continued

```
tccaaagatc cttagctcaa gagcatggaa tagagactcc caagtatctg gctgatttgt      360
ttgattataa aaccaagaga tttatagaag ttggaataac aaaaggattg gctgatgatt      420
acttttggaa aaagaaagaa aagctgggaa atagcatgga actgatgata ttcagctaca      480
atcaagacta ttcgttaagt aatgaatcct cattggatga ggaagggaaa gggagagtgc      540
taagcagact cacagaactt caggctgaat taagtctgaa aaacctatgg caagttctca      600
taggagaaga agatgttgaa aagggaattg actttaaact tggacaaaca atatctagac      660
taagggatat atctgttcca gctggtttct ccaattttga aggaatgagg agctacatag      720
acaatataga cccgaaagga gcaatagaga gaaatctagc aaggatgtct cccttagtat      780
cagtcacacc taaaaagttg aaatgggagg acctaagacc aataggggcct cacatttaca      840 accatgagct accagaagtt ccatataatg cctttcttct aatgtctgat gaactggggc      900
tggccaatat gactgaggga aagtccaaaa aaccgaagac attagccaaa gaatgtctag      960
aaaagtactc aacactacgg gatcaaactg acccaatatt aataatgaaa agcgaaaaag     1020
ctaacgaaaa tttcctatgg aagctttgga gagactgtgt aaatacaata agtaatgagg     1080
aaatgagtaa cgagttacag aaaaccaatt atgccaagtg gccacaggg gatggattaa      1140 cataccagaa aataatgaaa gaagtagcaa tagatgacga acaatgtgc caagaagagc      1200 ctaaaatccc taacaaatgt agagtggctg cttgggttca aacagagatg aatctattga     1260
gcactctgac aagtaaaaaa gctctggacc taccagaaat agggccagac gtagcacccg     1320
tggagcatgt agggagtgaa agaaggaaat actttgttaa tgaaatcaac tactgtaagg     1380
cctctacagt tatgatgaag tatgtgcttt ttcacacttc attgttgaat gaaagcaatg     1440
ccagcatggg aaaatacaaa gtaataccaa taaccaatag agtagtaaat gaaaaaggag     1500
aaagtttcga catgctctat ggtctggcgg ttaaaggaca atctcatctg aggggagata     1560
ctgatgttgt aacagttgta actttcgaat ttagtagtac agaccccaga gtggactcag     1620
gaaagtggcc aaaatatact gtgtttagga ttggctcccct atttgtgagt gggagggaaa     1680
agtctgtgta cctatattgc cgagtgaatg cacaaataa gatccaaatg aaatggggaa      1740
tggaagctag aagatgtctg cttcaatcaa tgcaacaaat ggaagcaatt gttgaacaag     1800
aatcatcgat acaaggatat gacatgacca aagcttgttt caagggagac agagtaaata     1860
gccccaaaac tttcagtatt ggaactcaag aaggaaaact agtaaaagga tcctttggaa     1920
aagcactaag agtaatattt actaaatgtt gatgcacta tgtatttgga aatgcccaat      1980
tggaggggtt tagtgccgag tctaggagac ttctactgtt gattcaagca ttaaaggaca     2040
gaaagggccc ttgggtgttc gacttagagg aatgtattc tggaatagaa gaatgtatta     2100
gtaacaaccc ttgggtaata cagagtgcat actggttcaa tgaatggttg ggcttttgaaa    2160 aggagggag taaagtatta gaatcagtag atgaaataat ggatgaataa aaggacatag     2220
tactcaattt agtactattt tgttcattat gtatctaaac atccaataaa aaggacaaag     2280
aattaaaaat gcacgtgttt ctact                                           2305
```

<210> SEQ ID NO 22
<211> LENGTH: 1882
<212> TYPE: DNA
<213> ORGANISM: Influenza B/Vienna/1/99/ca

<400> SEQUENCE: 22

```
agcagaagca gagcattttc taatatccac aaaaatgaagg caataattgt actactcatg       60
gtagtaacat ccaatgcaga tcgaatctgc actgggataa catcgtcaaa ctcacctcat      120
```

| | |
|---|---:|
| gtggtcaaaa cagctactca aggggaggtc aatgtgactg gtgcgatacc actgacaaca | 180 |
| acaccaacaa atctcatttt tgcaaatctc aaggaacaa agaccagagg gaaactatgc | 240 |
| ccaacctgtc tcaactgcac agatctggat gtggccttgg gcagaccaat gtgtgtgggg | 300 |
| atcacacctt cggcaaaagc ttcaatactc cacgaagtca gacctgttac atccggatgc | 360 |
| tttcctataa tgcacgacag aacaaaaatc agacagctac ccaatcttct cagaggatat | 420 |
| gaaaaaatca gattatcaac ccaaaacgtt atcaacacag aaaaggcacc aggaggaccc | 480 |
| tacagacttg gaacttcagg atcttgccct aacgctacca gtaaaagcgg attttttcgca | 540 |
| acaatggctt gggctgtccc aagggacaac aacaaaacag caacgaatcc actaacagta | 600 |
| gaagtaccac acatctgtac aaaagaagaa gaccaaatta ctgtttgggg gttccattct | 660 |
| gataacaaaa cccaaatgaa aaacctctat ggagactcaa atcctcaaaa gttcacctca | 720 |
| tctgctaatg gataaccac acattatgtt tctcagattg gcggcttccc ggaccaaaca | 780 |
| gaagacggag ggctaccaca agcggcaga attgttgttg attacatggt gcaaaaacct | 840 |
| gggaaaacag gaacaattgt ctatcaaaga gggattttgt tgcctcaaaa ggtgtggtgc | 900 |
| gcgagtggca ggagcaaagt aataaaaggg tccttgcctt taattggtga agcagattgc | 960 |
| cttcacgaaa atacggtgg attaaacaaa agcaagcctt actacacagg agaacatgca | 1020 |
| aaagccatag gaaattgccc aatatgggtg aaaacacctt gaagcttgc caatggaacc | 1080 |
| aaatatagac ctcctgcaaa actattaaag gaaggggtt tcttcggagc tattgctggt | 1140 |
| ttcttagaag gaggatggga aggaatgatt gcaggttggc acggatacac atctcacgga | 1200 |
| gcacatggag tggcagtggc agcagacctt aagagtacgc aagaagccat aaacaagata | 1260 |
| acaaaaaatc tcaattcttt gagtgagcta gaagtaaata accttcaaag actaagtggt | 1320 |
| gccatggatg aactccataa cgaaatactc gagctggatg agaaagtgga tgatctcaga | 1380 |
| gctgacacaa taagctcaca aatagaactt gcagtcttgc tttccaacga aggaataata | 1440 |
| aacagtgaag atgagcatct attggcactt gagagaaaac taaagaaaat gctgggtccc | 1500 |
| tctgctgtag acatagggaa tggatgcttc gaaaccaaac acaagtgcaa ccagacctgc | 1560 |
| ttagacagga tagctgctgg cacctttaat gcagaagaat tttctcttcc cacttttgat | 1620 |
| tcactgaaca ttactgctgc atcttttaaat gatgatggat tggataacca tactatactg | 1680 |
| ctctactact caactgctgc ttctagtttg gctgtaacat tgatgatagc tattttttatt | 1740 |
| gtttatatga tctccagaga caatgtttct tgctccatct gtctataagg aaaattaagc | 1800 |
| cctgtatttt cctttattgt ggtgcttgtt tgcttgttat cattacaaag aaacgttatt | 1860 |
| gaaaaatgct cttgttacta ct | 1882 |

<210> SEQ ID NO 23
<211> LENGTH: 1844
<212> TYPE: DNA
<213> ORGANISM: Influenza B/Vienna/1/99/ca

<400> SEQUENCE: 23

| | |
|---|---:|
| agcagaagca cagcattttc ttgtgaactt caagtaccag taaaagaact gaaaatcaaa | 60 |
| atgtccaaca tggatattga cggtatcaac actgggacaa ttgacaaaac accggaagaa | 120 |
| ataactttg gaccagtgg gacaaccaga ccaatcatca gaccagcaac ccttgcccca | 180 |
| ccaagcaaca aacgaacccg taaccccatcc ccggaaagag caaccacaag cagtgaagct | 240 |
| gatgtcggga ggaaaaccca aagaaacag accccgacag agataaagaa gagcgtctac | 300 |

```
aacatggtag tgaaactggg cgaattctac aaccagatga tggtcaaagc tggactcaac    360
gatgacatgg agagaaacct aatccaaaat gcgcatgctg tggaaagaat tctattggct    420
gccactgatg acaagaaaac tgaattccag aagaaaaaga ataccagaga tgtcaaagaa    480
gggaaagaag aaatagatca acacaaaaca ggaggcacct tttacaagat ggtaagagat    540
gataaaacca tctacttcag ccctataaga attacctttt taaaagaaga ggtgaaaaca    600
atgtacaaaa ccaccatggg gagtgatggc ttcagtggac taaatcacat aatgattggg    660
cattcacaga tgaatgatgt ctgtttccaa agatcaaagg cactaaaaag agttggactt    720 gaccccttcat taatcagtac ctttgcggga agcacaatcc ccagaagatc aggtgcaact    780
ggtgttgcaa tcaaaggagg tggaacttta gtggctgaag ccattcgatt tataggaaga    840
gcaatggcag acagagggct attgagagac atcaaagcca agactgccta tgaaaagatt    900
cttctgaatc taaaaaacaa atgctctgcg ccccaacaaa aggctctagt tgatcaagtg    960
atcggaagta gaaatccagg gattgcagac attgaagatc taacccctgct tgctcgtagt   1020 atggtcgttg ttaggccctc tgtggcgagc aaagtggtgc ttcccataag catttacgcc   1080
aaaatacctc aactagggtt caatgttgaa gagtactcta tggttgggta cgaagccatg   1140
gctctttaca atatggcaac acctgtttcc atattaagaa tgggagatga tgcaaaagat   1200
aagtcgcaat tattcttcat gtcttgcttc ggagctgcct atgaagacct gagagttttg   1260
tctgcattaa caggcacaga attcaagcct agatcagcat aaaaatgcaa gggtttccat   1320
gttccagcaa aggaacaggt ggaaggaatg ggggcagctc tgatgtccat caagctccag   1380
ttttgggctc caatgaccag atctggggg aacgaagtag gtggagacgg agggtctggc   1440
caaataagct gcagcccagt gtttgcagtg gaaagaccta ttgctctaag caagcaagct   1500
gtaagaagaa tgctgtcaat gaatattgag ggacgtgatg cagatgtcaa aggaaatcta   1560
ctcaagatga tgaatgactc aatggctaag aaaaccagtg gaaatgcttt cattgggaag   1620
aaaatgtttc aaatatcaga caaaaacaaa accaatcccg ttgaaattcc aattaagcag   1680
accatcccca atttcttctt tgggagggac acagcagagg attatgatga cctcgattat   1740
taaagcaaca aaatagacac tatgactgtg attgtttcaa tacgttttgga atgtgggtgt   1800 ttattcttat taaataaat ataaaaaatg ctgttgtttc tact                      1844
```

<210> SEQ ID NO 24
<211> LENGTH: 1557
<212> TYPE: DNA
<213> ORGANISM: Influenza B/Vienna/1/99/ca

<400> SEQUENCE: 24

```
agcagaagca gagcatcttc tcaaaactga ggcaaatagg ccaaaaatga acaatgctac    60
cttcaactat acaaacgtta accctattcc tcacatcagg gggagtgtta ttatcactat   120
atgtgtcagc ttcactgtca tacttattat attcggatat attgctaaaa tttcaccaa    180 cagaaataac tgcaccaaca atgccattgg attgtgcaaa cgcatcaaat gttcaggctg   240
tgaaccgttc tgcaacaaaa ggggtgcac ttcttctccc agaaccggag tggacatacc    300
cgcgtttatc ttgcccgggc tcaacctttc agaaagcact cctaattagc cctcatagat    360
tcggagaaac caaggaaac tcagctccct tgataataag ggaacctttt attgcttgtg    420
gaccaaagga atgcaaacac tttgctctaa cccattatgc agcccaacca ggggatact    480 acaatggaac aagagaagac agaaacaagc tgaggcatct aatttcagtc aaattgggca   540
aaatcccaac agtagaaaac tccatttttcc acatggcagc atggagcggg tccgcatgcc   600
```

| | |
|---|---|
| atgatggtaa agaatggaca tatatcggag ttgatggccc tgacagtaat gcattgctca | 660 |
| aaataaaata tggagaagca tatactgaca cataccattc ctatgcaaac aacatcctaa | 720 |
| gaacacaaga aagtgcctgc aattgcatcg ggggaaattg ttatcttatg ataactgatg | 780 |
| gctcagcttc aggtattagt gaatgcagat ttcttaagat tcaagagggc cgaataataa | 840 |
| aagaaatatt tccaacagga agagtagaac atactgaaga atgcacatgc ggatttgcca | 900 |
| gcaataaaac catagaatgt gcctgtagag ataacagtta cacagcaaaa agaccctttg | 960 |
| tcaaattaaa tgtggagact gatacagcag aaataagatt gatgtgcaca gagacttact | 1020 |
| tggacacccc cagaccagat gatggaagca taacagggcc ttgtgaatct aatggggata | 1080 |
| aagggagtgg aggcatcaag ggaggatttg ttcatcaaag aatggcatcc aagactggaa | 1140 |
| ggtggtactc tcgaacaatg tctaaaacta aaaggatggg gatgggactg tatgtcaagt | 1200 |
| atgatgagaa cccatggact gacagtgatg cccttgctct tagtggagta atggtttcaa | 1260 |
| tggaagaacc tggttggtac tcctttggct tcgaaataaa agataagaaa tgtgatgtcc | 1320 |
| cctgtattgg gatagagatg gtacatgatg gtggaaagga gacttggcac tcagcagcaa | 1380 |
| cagccattta ctgtttaatg ggctcaggac aactgctatg ggacactgtc acaggtgtta | 1440 |
| atatggctct gtaatggagg aatggttgag tctgttctaa acccttt gtt cctattttgt | 1500 |
| ttgaacaatt gtccttactg aacttaattg tttctgaaaa atgctcttgt tactact | 1557 |

<210> SEQ ID NO 25
<211> LENGTH: 1190
<212> TYPE: DNA
<213> ORGANISM: Influenza B/Vienna/1/99/ca

<400> SEQUENCE: 25

| | |
|---|---|
| agcagaagca cgcactttct taagatgtcg ctgtttggag acacaattgc ctacctgctt | 60 |
| tcattgacag aagatggaga aggcaaagca gaactagcag aaaaattaca ctgttggttc | 120 |
| ggtgggaaag aatttgacct agactctgcc ttggaatgga taaaaacaa agatgctta | 180 |
| actgatatac aaaagcact aattggtgcc tctatctgct tttaaaacc caagaccag | 240 |
| gaaagaaaaa gaagattcat cacagagccc ctatcaggaa tgggaacaac agcaacaaaa | 300 |
| aagaaaggcc tgattctagc tgagagaaaa atgagaagat gtgtgagctt catgaagca | 360 |
| tttgaaatag cagaaggcca tgaaagctca gcgctactat attgtctcat ggtcatgtac | 420 |
| ctgaatcctg gaaattattc aatgcaagta aaactaggaa cgctctgtgc tttgtgcgag | 480 |
| aaacaagcat cacattcaca cagggctcat agcagagcag cgagatcttc agtgcccgga | 540 |
| gtgagacgag aaatgcagat ggtctcagct atgaacacag caaaaacaat gaatggaatg | 600 |
| ggaaaaggag aagacgtcca aaaactggca gaaagagctgc aaagcaacat ggagtactg | 660 |
| agatctcttg gggcaagtca aaagaatggg aaggaattg caaggatgt aatggaagtg | 720 |
| ctaaagcaga gctctatggg aaattcagct cttgtgaaga aatatctata atgctcgaac | 780 |
| catttcagat tctttcaatt tgttcttta tcttatcagc tctccatttc gtggcttgga | 840 |
| caatagggca tttgaatcaa ataaaagag gagtaaacat gaaaatacga ataaaaagtc | 900 |
| caaacaaaga gacaataaac agagaggtat caattttgag acacagttac caaaagaaa | 960 |
| tccaggccaa agaaacaatg aaggaagtac tctctgacaa catggaggta ttgggtgacc | 1020 |
| acatagtaat tgagggggctt tctgccgaag agataataaa aatgggtgaa acagttttgg | 1080 |
| agatagaaga attgcattaa attcaatttt tactgtattt cttactatgc atttaagcaa | 1140 |

```
attgtaatca atgtcagcaa ataaactgga aaaagtgcgt tgtttctact            1190
```

<210> SEQ ID NO 26
<211> LENGTH: 1097
<212> TYPE: DNA
<213> ORGANISM: Influenza B/Vienna/1/99/ca

<400> SEQUENCE: 26

```
agcagaagca gagcatttgt ttagtcactg gcaaacagga aaaatggcga acaacataac     60
cacaacacaa attgaggtgg gtccgggagc aaccaatgcc accataaact ttgaaacagg    120
aattctggag tgctatgaaa ggctttcatg caaagagcc cttgactacc ctggtcaaga     180
ccgcctaaac agactaaaga gaaaattaga gtcaagaata agactcaca acaaaagtga     240
gcctgaaagt aaaaggatgt ctcttgaaga gaggaaagca attggagtaa aaatgatgaa    300
agtactccta tttatgaatc catctgctgg aattgaaggg tttgagccat actatatgaa    360
aagttcctca aatagcaact gtccgaaata caattggacc gattaccctt caacaccagg    420
gaggtgcctt gatgacatag aagaagaacc agaggatgtt gatggcccaa ctgaaatagt    480
attaagggac atgaacaaca agatgcaag gcaaagata aagaggaag taaacactca      540
gaaagaaggg aagttccgtt tgacaataaa aagggatata cgtaatgtat tgtccttgag    600
agtgttggta acggaacat tcctcaaaca ccccaatgga tacaagtcct tatcaactct    660
gcatagattg aatgcatatg accagagtgg aaggcttgtt gctaaacttg ttgctactga    720
tgatcttaca gtggaggatg aagaagatgg ccatcggatc ctcaactcac tcttcgagcg    780
tcttaatgaa ggacattcaa agccaattcg agcagctgaa actgcggtgg gagtcttatc    840
ccaatttggt caagagcacc gattatcacc agaagaggga gacaattaaa ctggtcacag    900
aagaactta tctttaagt aaaagaattg atgataacat attgttccac aaaacagtaa       960
tagctaacag ctccataata gctgacatgg ttgtatcatt atcattatta gaaacattgt   1020
atgaaatgaa ggatgtggtt gaagtgtaca gcaggcagtg cttgtgaatt taaaataaaa   1080
atcctcttgt tactact                                                   1097
```

<210> SEQ ID NO 27
<211> LENGTH: 770
<212> TYPE: PRT
<213> ORGANISM: Influenza B/Vienna/1/99/ca

<400> SEQUENCE: 27

```
Met Thr Leu Ala Lys Ile Glu Leu Leu Lys Gln Leu Leu Arg Asp Asn
1               5                   10                  15

Glu Ala Lys Thr Val Leu Lys Gln Thr Thr Val Asp Gln Tyr Asn Ile
            20                  25                  30

Ile Arg Lys Phe Asn Thr Ser Arg Ile Glu Lys Asn Pro Ser Leu Arg
        35                  40                  45

Met Lys Trp Ala Met Cys Ser Asn Phe Pro Leu Ala Leu Thr Lys Gly
    50                  55                  60

Asp Met Ala Asn Arg Ile Pro Leu Glu Tyr Lys Gly Ile Gln Leu Lys
65                  70                  75                  80

Thr Asn Ala Glu Asp Ile Gly Thr Lys Gly Gln Met Cys Ser Ile Ala
            85                  90                  95

Ala Val Thr Trp Trp Asn Thr Tyr Gly Pro Ile Gly Asp Thr Glu Gly
            100                 105                 110

Phe Glu Lys Val Tyr Glu Ser Phe Phe Leu Arg Lys Met Arg Leu Asp
        115                 120                 125
```

```
Asn Ala Thr Trp Gly Arg Ile Thr Phe Gly Pro Val Glu Arg Val Arg
    130                 135                 140

Lys Arg Val Leu Leu Asn Pro Leu Thr Lys Glu Met Pro Pro Asp Glu
145                 150                 155                 160

Ala Ser Asn Val Ile Met Glu Ile Leu Phe Pro Lys Glu Ala Gly Ile
                165                 170                 175

Pro Arg Glu Ser Thr Trp Ile His Arg Glu Leu Ile Lys Glu Lys Arg
            180                 185                 190

Glu Lys Leu Lys Gly Thr Met Ile Thr Pro Ile Val Leu Ala Tyr Met
        195                 200                 205

Leu Glu Arg Glu Leu Val Ala Arg Arg Phe Leu Pro Val Ala Gly
    210                 215                 220

Ala Thr Ser Ala Glu Phe Ile Glu Met Leu His Cys Leu Gln Gly Glu
225                 230                 235                 240

Asn Trp Arg Gln Ile Tyr His Pro Gly Gly Asn Lys Leu Thr Glu Ser
                245                 250                 255

Arg Ser Gln Ser Met Ile Val Ala Cys Arg Lys Ile Ile Arg Arg Ser
            260                 265                 270

Ile Val Ala Ser Asn Pro Leu Glu Leu Ala Val Glu Ile Ala Asn Lys
        275                 280                 285

Thr Val Ile Asp Thr Glu Pro Leu Lys Ser Cys Leu Thr Ala Ile Asp
    290                 295                 300

Gly Gly Asp Val Ala Cys Asp Ile Ile Arg Ala Ala Leu Gly Leu Lys
305                 310                 315                 320

Ile Arg Gln Arg Gln Arg Phe Gly Arg Leu Glu Leu Lys Arg Ile Ser
                325                 330                 335

Gly Arg Gly Phe Lys Asn Asp Glu Glu Ile Leu Ile Gly Asn Gly Thr
            340                 345                 350

Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Arg Met Glu
    370                 375                 380

Lys Leu Leu Ile Asn Ser Ala Lys Lys Glu Asp Met Lys Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Asn Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Leu Met Asn Ala Ser Asp Tyr Thr Leu Lys Gly Val Val
465                 470                 475                 480

Val Thr Lys Asn Val Ile Asp Asp Phe Ser Ser Thr Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540
```

```
Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
            565                 570                 575

Ala Phe Glu Ala Phe Glu Ser Ile Ile Pro Gln Lys Met Ala Gly Gln
                580                 585                 590

Tyr Ser Gly Phe Ala Arg Ala Val Leu Lys Gln Met Arg Asp Gln Glu
            595                 600                 605

Val Met Lys Thr Asp Gln Phe Ile Lys Leu Leu Pro Phe Cys Phe Ser
        610                 615                 620

Pro Pro Lys Leu Arg Ser Asn Gly Glu Pro Tyr Gln Phe Leu Arg Leu
625                 630                 635                 640

Val Leu Lys Gly Gly Gly Glu Asn Phe Ile Glu Val Arg Lys Gly Ser
                645                 650                 655

Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
        675                 680                 685

Ser Met Gly Asn Ala Val Leu Ala Gly Phe Leu Val Ser Gly Lys Tyr
    690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735

Lys Val Val Lys Arg Lys Arg Tyr Ser Ala Leu Ser Asn Asp Ile Ser
            740                 745                 750

Gln Gly Ile Lys Arg Gln Arg Met Thr Val Glu Ser Met Gly Trp Ala
        755                 760                 765

Leu Ser
    770

<210> SEQ ID NO 28
<211> LENGTH: 752
<212> TYPE: PRT
<213> ORGANISM: Influenza B/Vienna/1/99/ca

<400> SEQUENCE: 28

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
            20                  25                  30

Gly Thr Gly Thr Gly His Thr Ile Asp Thr Val Ile Arg Thr His Glu
        35                  40                  45

Tyr Ser Asn Lys Gly Lys Gln Tyr Val Ser Asp Ile Thr Gly Cys Thr
    50                  55                  60

Met Val Asp Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140
```

-continued

```
Thr Thr Ile Thr Ser Phe Arg Leu Asn Asp Leu Asn Gly Ala Asp Lys
145                 150                 155                 160

Gly Gly Leu Val Pro Phe Cys Gln Asp Ile Ile Asp Ser Leu Asp Lys
                165                 170                 175

Pro Glu Met Thr Phe Phe Ser Val Lys Asn Ile Lys Lys Lys Phe Pro
            180                 185                 190

Ala Lys Asn Arg Lys Gly Phe Leu Ile Lys Arg Ile Pro Met Lys Val
        195                 200                 205

Lys Asp Arg Ile Ser Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
                260                 265                 270

Val Gly Gly Asn Glu Lys Lys Ala Lys Leu Ser Asn Ala Val Ala Lys
            275                 280                 285

Met Leu Ser Asn Cys Pro Pro Gly Gly Ile Ser Met Thr Val Thr Gly
        290                 295                 300

Asp Asn Thr Lys Trp Asn Glu Cys Leu Asn Pro Arg Val Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
                340                 345                 350

Lys Gly Phe Met Ile Thr Ser Lys Thr Lys Arg Leu Lys Ala Gln Ile
            355                 360                 365

Pro Cys Pro Asp Leu Phe Ser Ile Pro Leu Glu Arg Tyr Asn Glu Glu
        370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
                420                 425                 430

Lys Glu Tyr Leu Trp Asp Gly Leu Gln Ser Ser Asp Asp Phe Ala Leu
            435                 440                 445

Phe Val Asn Ala Lys Asp Glu Glu Thr Cys Met Glu Gly Ile Asn Asp
450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Ile Pro Ser Phe Gly
            500                 505                 510

Val Ala Gly Val Asn Glu Ser Ala Asp Met Ala Ile Gly Met Thr Ile
            515                 520                 525

Ile Lys Asn Asn Met Ile Asn Asn Gly Met Gly Pro Ala Thr Ala Gln
        530                 535                 540

Thr Ala Ile Gln Leu Phe Ile Ala Asp Tyr Arg Tyr Thr Tyr Lys Cys
545                 550                 555                 560
```

His Arg Gly Asp Ser Lys Val Glu Gly Lys Arg Met Lys Ile Ile Lys
            565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
            595                 600                 605

Val Leu Lys Tyr Asn Leu Met Asp Pro Glu Tyr Lys Gly Arg Leu Leu
            610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Lys Lys Met Asp Tyr
            645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
            675                 680                 685

Ala Lys Cys Cys Asn Leu Phe Glu Ala Cys Phe Asn Ser Ala Ser Tyr
            690                 695                 700

Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
            725                 730                 735

Asp Asp Phe Glu Lys Ala Met Ala His Leu Gly Glu Ile Gly Tyr Thr
            740                 745                 750

<210> SEQ ID NO 29
<211> LENGTH: 726
<212> TYPE: PRT
<213> ORGANISM: Influenza B/Vienna/1/99/ca

<400> SEQUENCE: 29

Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
            35                  40                  45

Ser Asp Met Asn Phe Leu Asp Glu Glu Gly Lys Ala Tyr Thr Ala Leu
        50                  55                  60

Glu Gly Gln Gly Lys Glu Gln Asn Leu Arg Pro Gln Tyr Glu Val Ile
65                  70                  75                  80

Glu Gly Met Pro Arg Thr Ile Ala Trp Met Val Gln Arg Ser Leu Ala
            85                  90                  95

Gln Glu His Gly Ile Glu Thr Pro Lys Tyr Leu Ala Asp Leu Phe Asp
            100                 105                 110

Tyr Lys Thr Lys Arg Phe Ile Glu Val Gly Ile Thr Lys Gly Leu Ala
        115                 120                 125

Asp Asp Tyr Phe Trp Lys Lys Lys Glu Lys Leu Gly Asn Ser Met Glu
    130                 135                 140

Leu Met Ile Phe Ser Tyr Asn Gln Asp Tyr Ser Leu Ser Asn Glu Ser
145                 150                 155                 160

Ser Leu Asp Glu Glu Gly Lys Gly Arg Val Leu Ser Arg Leu Thr Glu
            165                 170                 175

Leu Gln Ala Glu Leu Ser Leu Lys Asn Leu Trp Gln Val Leu Ile Gly
            180                 185                 190

-continued

```
Glu Glu Asp Val Glu Lys Gly Ile Asp Phe Lys Leu Gly Gln Thr Ile
        195                 200                 205
Ser Arg Leu Arg Asp Ile Ser Val Pro Ala Gly Phe Ser Asn Phe Glu
    210                 215                 220
Gly Met Arg Ser Tyr Ile Asp Asn Ile Asp Pro Lys Gly Ala Ile Glu
225                 230                 235                 240
Arg Asn Leu Ala Arg Met Ser Pro Leu Val Ser Val Thr Pro Lys Lys
                245                 250                 255
Leu Lys Trp Glu Asp Leu Arg Pro Ile Gly Pro His Ile Tyr Asn His
            260                 265                 270
Glu Leu Pro Glu Val Pro Tyr Asn Ala Phe Leu Leu Met Ser Asp Glu
        275                 280                 285
Leu Gly Leu Ala Asn Met Thr Glu Gly Lys Ser Lys Lys Pro Lys Thr
    290                 295                 300
Leu Ala Lys Glu Cys Leu Glu Lys Tyr Ser Thr Leu Arg Asp Gln Thr
305                 310                 315                 320
Asp Pro Ile Leu Ile Met Lys Ser Glu Lys Ala Asn Glu Asn Phe Leu
                325                 330                 335
Trp Lys Leu Trp Arg Asp Cys Val Asn Thr Ile Ser Asn Glu Glu Met
            340                 345                 350
Ser Asn Glu Leu Gln Lys Thr Asn Tyr Ala Lys Trp Ala Thr Gly Asp
        355                 360                 365
Gly Leu Thr Tyr Gln Lys Ile Met Lys Glu Val Ala Ile Asp Asp Glu
    370                 375                 380
Thr Met Cys Gln Glu Glu Pro Lys Ile Pro Asn Lys Cys Arg Val Ala
385                 390                 395                 400
Ala Trp Val Gln Thr Glu Met Asn Leu Leu Ser Thr Leu Thr Ser Lys
                405                 410                 415
Lys Ala Leu Asp Leu Pro Glu Ile Gly Pro Asp Val Ala Pro Val Glu
            420                 425                 430
His Val Gly Ser Glu Arg Arg Lys Tyr Phe Val Asn Glu Ile Asn Tyr
        435                 440                 445
Cys Lys Ala Ser Thr Val Met Met Lys Tyr Val Leu Phe His Thr Ser
    450                 455                 460
Leu Leu Asn Glu Ser Asn Ala Ser Met Gly Lys Tyr Lys Val Ile Pro
465                 470                 475                 480
Ile Thr Asn Arg Val Val Asn Glu Lys Gly Glu Ser Phe Asp Met Leu
                485                 490                 495
Tyr Gly Leu Ala Val Lys Gly Gln Ser His Leu Arg Gly Asp Thr Asp
            500                 505                 510
Val Val Thr Val Val Thr Phe Glu Phe Ser Ser Thr Asp Pro Arg Val
        515                 520                 525
Asp Ser Gly Lys Trp Pro Lys Tyr Thr Val Phe Arg Ile Gly Ser Leu
    530                 535                 540
Phe Val Ser Gly Arg Glu Lys Ser Val Tyr Leu Tyr Cys Arg Val Asn
545                 550                 555                 560
Gly Thr Asn Lys Ile Gln Met Lys Trp Gly Met Glu Ala Arg Arg Cys
                565                 570                 575
Leu Leu Gln Ser Met Gln Met Glu Ala Ile Val Glu Gln Glu Ser
            580                 585                 590
Ser Ile Gln Gly Tyr Asp Met Thr Lys Ala Cys Phe Lys Gly Asp Arg
        595                 600                 605
```

```
Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Ile Gln Ala Leu Lys Asp Arg Lys
                660                 665                 670

Gly Pro Trp Val Phe Asp Leu Glu Gly Met Tyr Ser Gly Ile Glu Glu
            675                 680                 685

Cys Ile Ser Asn Asn Pro Trp Val Ile Gln Ser Ala Tyr Trp Phe Asn
        690                 695                 700

Glu Trp Leu Gly Phe Glu Lys Glu Gly Ser Lys Val Leu Glu Ser Val
705                 710                 715                 720

Asp Glu Ile Met Asp Glu
                725

<210> SEQ ID NO 30
<211> LENGTH: 584
<212> TYPE: PRT
<213> ORGANISM: Influenza B/Vienna/1/99/ca

<400> SEQUENCE: 30

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Ala Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Thr Cys Leu Asn Cys Thr Asp Leu Asp Val
65                  70                  75                  80

Ala Leu Gly Arg Pro Met Cys Val Gly Ile Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Lys Ile Arg Leu Ser Thr Gln Asn Val Ile Asn Thr Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Arg Asp Asn Asn Lys Thr Ala Thr Asn Pro Leu Thr Val Glu Val Pro
            180                 185                 190

His Ile Cys Thr Lys Glu Glu Asp Gln Ile Thr Val Trp Gly Phe His
        195                 200                 205

Ser Asp Asn Lys Thr Gln Met Lys Asn Leu Tyr Gly Asp Ser Asn Pro
    210                 215                 220

Gln Lys Phe Thr Ser Ser Ala Asn Gly Ile Thr Thr His Tyr Val Ser
225                 230                 235                 240

Gln Ile Gly Gly Phe Pro Asp Gln Thr Glu Asp Gly Gly Leu Pro Gln
                245                 250                 255
```

Ser Gly Arg Ile Val Val Asp Tyr Met Val Gln Lys Pro Gly Lys Thr
            260                 265                 270

Gly Thr Ile Val Tyr Gln Arg Gly Ile Leu Leu Pro Gln Lys Val Trp
        275                 280                 285

Cys Ala Ser Gly Arg Ser Lys Val Ile Lys Gly Ser Leu Pro Leu Ile
        290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
            325                 330                 335

Ile Trp Val Lys Thr Pro Leu Lys Leu Ala Asn Gly Thr Lys Tyr Arg
        340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
        370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
            405                 410                 415

Ser Glu Leu Glu Val Asn Asn Leu Gln Arg Leu Ser Gly Ala Met Asp
        420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
            485                 490                 495

Gly Cys Phe Glu Thr Lys His Lys Cys Asn Gln Thr Cys Leu Asp Arg
        500                 505                 510

Ile Ala Ala Gly Thr Phe Asn Ala Glu Glu Phe Ser Leu Pro Thr Phe
        515                 520                 525

Asp Ser Leu Asn Ile Thr Ala Ala Ser Leu Asn Asp Asp Gly Leu Asp
        530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Ile Val Tyr Met Ile Ser Arg Asp
            565                 570                 575

Asn Val Ser Cys Ser Ile Cys Leu
            580

<210> SEQ ID NO 31
<211> LENGTH: 560
<212> TYPE: PRT
<213> ORGANISM: Influenza B/Vienna/1/99/ca

<400> SEQUENCE: 31

Met Ser Asn Met Asp Ile Asp Gly Ile Asn Thr Gly Thr Ile Asp Lys
1               5                   10                  15

Thr Pro Glu Glu Ile Thr Phe Gly Thr Ser Gly Thr Thr Arg Pro Ile
            20                  25                  30

Ile Arg Pro Ala Thr Leu Ala Pro Pro Ser Asn Lys Arg Thr Arg Asn

```
                35                  40                  45
Pro Ser Pro Glu Arg Ala Thr Thr Ser Ser Glu Ala Asp Val Gly Arg
 50                  55                  60

Lys Thr Gln Lys Lys Gln Thr Pro Thr Glu Ile Lys Lys Ser Val Tyr
 65                  70                  75                  80

Asn Met Val Val Lys Leu Gly Glu Phe Tyr Asn Gln Met Met Val Lys
                 85                  90                  95

Ala Gly Leu Asn Asp Asp Met Glu Arg Asn Leu Ile Gln Asn Ala His
                100                 105                 110

Ala Val Glu Arg Ile Leu Leu Ala Ala Thr Asp Lys Lys Thr Glu
            115                 120                 125

Phe Gln Lys Lys Lys Asn Thr Arg Asp Val Lys Glu Gly Lys Glu Glu
            130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
                180                 185                 190

Gly Leu Asn His Ile Met Ile Gly His Ser Gln Met Asn Asp Val Cys
                195                 200                 205

Phe Gln Arg Ser Lys Ala Leu Lys Arg Val Gly Leu Asp Pro Ser Leu
            210                 215                 220

Ile Ser Thr Phe Ala Gly Ser Thr Ile Pro Arg Arg Ser Gly Ala Thr
225                 230                 235                 240

Gly Val Ala Ile Lys Gly Gly Thr Leu Val Ala Glu Ala Ile Arg
                245                 250                 255

Phe Ile Gly Arg Ala Met Ala Asp Arg Gly Leu Leu Arg Asp Ile Lys
                260                 265                 270

Ala Lys Thr Ala Tyr Glu Lys Ile Leu Leu Asn Leu Lys Asn Lys Cys
            275                 280                 285

Ser Ala Pro Gln Gln Lys Ala Leu Val Asp Gln Val Ile Gly Ser Arg
            290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
                340                 345                 350

Ser Met Val Gly Tyr Glu Ala Met Ala Leu Tyr Asn Met Ala Thr Pro
                355                 360                 365

Val Ser Ile Leu Arg Met Gly Asp Asp Ala Lys Asp Lys Ser Gln Leu
            370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
                420                 425                 430

Ala Leu Met Ser Ile Lys Leu Gln Phe Trp Ala Pro Met Thr Arg Ser
            435                 440                 445

Gly Gly Asn Glu Val Gly Gly Asp Gly Gly Ser Gly Gln Ile Ser Cys
450                 455                 460
```

```
Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
            515                 520                 525

Asn Lys Thr Asn Pro Val Glu Ile Pro Ile Lys Gln Thr Ile Pro Asn
        530                 535                 540

Phe Phe Phe Gly Arg Asp Thr Ala Glu Asp Tyr Asp Asp Leu Asp Tyr
545                 550                 555                 560

<210> SEQ ID NO 32
<211> LENGTH: 100
<212> TYPE: PRT
<213> ORGANISM: Influenza B/Vienna/1/99/ca

<400> SEQUENCE: 32

Met Asn Asn Ala Thr Phe Asn Tyr Thr Asn Val Asn Pro Ile Pro His
1               5                   10                  15

Ile Arg Gly Ser Val Ile Ile Thr Ile Cys Val Ser Phe Thr Val Ile
            20                  25                  30

Leu Ile Ile Phe Gly Tyr Ile Ala Lys Ile Phe Thr Asn Arg Asn Asn
            35                  40                  45

Cys Thr Asn Asn Ala Ile Gly Leu Cys Lys Arg Ile Lys Cys Ser Gly
        50                  55                  60

Cys Glu Pro Phe Cys Asn Lys Arg Gly Asp Thr Ser Ser Pro Arg Thr
65                  70                  75                  80

Gly Val Asp Ile Pro Ala Phe Ile Leu Pro Gly Leu Asn Leu Ser Glu
                85                  90                  95

Ser Thr Pro Asn
            100

<210> SEQ ID NO 33
<211> LENGTH: 466
<212> TYPE: PRT
<213> ORGANISM: Influenza B/Vienna/1/99/ca

<400> SEQUENCE: 33

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
            35                  40                  45

Thr Met Pro Leu Asp Cys Ala Asn Ala Ser Asn Val Gln Ala Val Asn
        50                  55                  60

Arg Ser Ala Thr Lys Gly Val Thr Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
            115                 120                 125
```

His Phe Ala Leu Thr His Tyr Ala Ala Gln Pro Gly Gly Tyr Tyr Asn
            130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Ile Ser Glu Cys Arg Phe Leu Lys Ile
                245                 250                 255

Gln Glu Gly Arg Ile Ile Lys Glu Ile Phe Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
            340                 345                 350

Val His Gln Arg Met Ala Ser Lys Thr Gly Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Thr Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asn Met
    450                 455                 460

Ala Leu
465

<210> SEQ ID NO 34
<211> LENGTH: 248
<212> TYPE: PRT
<213> ORGANISM: Influenza B/Vienna/1/99/ca

<400> SEQUENCE: 34

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe

```
                    20                  25                  30
Gly Gly Lys Glu Phe Asp Leu Asp Ser Ala Leu Glu Trp Ile Lys Asn
             35                  40                  45

Lys Arg Cys Leu Thr Asp Ile Gln Lys Ala Leu Ile Gly Ala Ser Ile
         50                  55                  60

Cys Phe Leu Lys Pro Lys Asp Gln Glu Arg Lys Arg Phe Ile Thr
 65                  70                  75                  80

Glu Pro Leu Ser Gly Met Gly Thr Thr Ala Thr Lys Lys Lys Gly Leu
                     85                  90                  95

Ile Leu Ala Glu Arg Lys Met Arg Arg Cys Val Ser Phe His Glu Ala
                100                 105                 110

Phe Glu Ile Ala Glu Gly His Glu Ser Ser Ala Leu Leu Tyr Cys Leu
            115                 120                 125

Met Val Met Tyr Leu Asn Pro Gly Asn Tyr Ser Met Gln Val Lys Leu
        130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
                180                 185                 190

Gly Lys Gly Glu Asp Val Gln Lys Leu Ala Glu Glu Leu Gln Ser Asn
            195                 200                 205

Ile Gly Val Leu Arg Ser Leu Gly Ala Ser Gln Lys Asn Gly Glu Gly
        210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245

<210> SEQ ID NO 35
<211> LENGTH: 109
<212> TYPE: PRT
<213> ORGANISM: Influenza B/Vienna/1/99/ca

<400> SEQUENCE: 35

Met Leu Glu Pro Phe Gln Ile Leu Ser Ile Cys Ser Phe Ile Leu Ser
 1               5                  10                  15

Ala Leu His Phe Val Ala Trp Thr Ile Gly His Leu Asn Gln Ile Lys
            20                  25                  30

Arg Gly Val Asn Met Lys Ile Arg Ile Lys Ser Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Thr Met Lys Glu Val Leu Ser Asp Asn Met Glu Val
 65                  70                  75                  80

Leu Gly Asp His Ile Val Ile Glu Gly Leu Ser Ala Glu Glu Ile Ile
                 85                  90                  95

Lys Met Gly Glu Thr Val Leu Glu Ile Glu Glu Leu His
            100                 105

<210> SEQ ID NO 36
<211> LENGTH: 281
<212> TYPE: PRT
<213> ORGANISM: Influenza B/Vienna/1/99/ca
```

<400> SEQUENCE: 36

```
Met Ala Asn Asn Ile Thr Thr Thr Gln Ile Glu Val Gly Pro Gly Ala
1               5                   10                  15

Thr Asn Ala Thr Ile Asn Phe Glu Thr Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asn Pro Ser Ala Gly
                85                  90                  95

Ile Glu Gly Phe Glu Pro Tyr Tyr Met Lys Ser Ser Asn Ser Asn
                100                 105                 110

Cys Pro Lys Tyr Asn Trp Thr Asp Tyr Pro Ser Thr Pro Gly Arg Cys
            115                 120                 125

Leu Asp Asp Ile Glu Glu Glu Pro Glu Asp Val Asp Gly Pro Thr Glu
130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280
```

<210> SEQ ID NO 37
<211> LENGTH: 122
<212> TYPE: PRT
<213> ORGANISM: Influenza B/Vienna/1/99/ca

<400> SEQUENCE: 37

```
Met Ala Asn Asn Ile Thr Thr Thr Gln Ile Glu Trp Arg Met Lys Lys
1               5                   10                  15

Met Ala Ile Gly Ser Ser Thr His Ser Ser Ser Val Leu Met Lys Asp
            20                  25                  30

Ile Gln Ser Gln Phe Glu Gln Leu Lys Leu Arg Trp Glu Ser Tyr Pro
        35                  40                  45

Asn Leu Val Lys Ser Thr Asp Tyr His Gln Lys Arg Glu Thr Ile Lys
    50                  55                  60

Leu Val Thr Glu Glu Leu Tyr Leu Leu Ser Lys Arg Ile Asp Asp Asn
65                  70                  75                  80
```

```
-continued

Ile Leu Phe His Lys Thr Val Ile Ala Asn Ser Ser Ile Ile Ala Asp
            85              90              95

Met Val Val Ser Leu Ser Leu Leu Glu Thr Leu Tyr Glu Met Lys Asp
            100             105             110

Val Val Glu Val Tyr Ser Arg Gln Cys Leu
        115             120
```

LIVE ATTENUATED INFLUENZA VACCINE

TECHNICAL FIELD

The present invention is in the field of virology and vaccine development and relates to an improved method of manufacture of a viral vaccine, particularly of a whole-virus vaccine, preferably of an attenuated live vaccine and to vaccines obtainable by the method.

BACKGROUND OF THE INVENTION

The influenza hemagglutinin (HA) antigen is the major target for the protective immune responses of a host to the virus.

A common practice of recovering new viral isolates involves recovery from a nasal or throat swab or from a similar source, followed by cultivation of the isolates in embryonated chicken eggs. The virus adapts to its egg host and large scale production of the virus can be carried out in eggs. Such conventional methodology involving embryonated chicken eggs to produce Influenza vaccine is, however, extremely cumbersome, involving the handling of many thousands of eggs per week as well as extensive purification of the virus suspension derived from the allantoic fluid to ensure freedom from egg protein.

Another disadvantage in the use of chicken embryos for virus production lies in the fact that this substrate strongly favors the selection of virus variants that differ in their antigenic specificity from the wildtype virus and not rarely results in viruses that may not be suitable for vaccine production due to their altered phenotypes including, for instance, considerable reduction in immunogenicity.

Many attempts have therefore been undertaken in the art to utilize standard tissue culture technology with established mammalian cell lines, such as MDCK (Madin-Darby Canine Kidney) or Vero (African Green Monkey Kidney) cells, for virus production, particularly influenza virus production.

One of the difficulties in growing influenza strains in tissue cell culture arises from the necessity for proteolytic cleavage of the influenza hemagglutinin in the host cell. Cleavage of the virus HA precursor into the HA1 and HA2 subfragments, although not necessary for the assembly of the viral elements to form a complete virion, is required, however, to render the virion infective, i.e. to enable it to infect a new cell.

It has been reported. (e.g. Lazarowitz et al., "Enhancement of the Infectivity of Influenza and B Viruses by Proteolytic Cleavage of the Hemagglutinin Polypeptide", Virology, 68:440-454, 1975) that the limited replication of several influenza A strains in standard cell cultures could be overcome by the addition of proteases like trypsin to the tissue culture medium. Yet, there remained difficulties in some cases, for instance when using Vero cells.

Kaverian and Webster (J Virol 69/4:2700-2703, 1995) report that in Vero cell cultures, and less pronounced in MDCK, swine kidney, or rhesus monkey kidney cell cultures, the trypsin activity in the medium rapidly decreased from the onset of incubation resulting in the failure of virus accumulation in the medium due to the lack of production of a sufficient number of infective virions. They concluded that a trypsin inhibiting factor was released from the Vero cells. They further showed that by repeated addition of trypsin reproduction of virus could be resumed and maintained for a number of reproduction cycles resulting in a much better virus yield.

Another way for efficient vaccine production was reported in U.S. Pat. No. 5,753,489 wherein serum-free medium was used for virus propagation in a number of different mammalian cells including MDCK and Vero cells. The method disclosed therein comprises growing vertebrate cells in serum-free medium, infecting the cell culture with a virus, incubating the cell culture infected with the virus, removing a portion of the virus-containing medium and contacting this portion. with a protease, thereafter adding to that portion a protease inhibitor and returning that portion to the cell culture. It is preferred therein to provide the steps of growing, infecting and incubating in a first vessel and the steps of trypsin-contacting and inhibitor-adding are performed in a second vessel connected with the first vessel in a loop so that the steps o can be performed in a closed cycle. This system allows to use trypsin or other proteolytic enzymes at much higher concentrations than those normally tolerated by cells in culture.

EP 0870508 reports a method to produce a viral antigen vaccine comprising infecting an animal cell line, optionally a Vero cell line, with virus, propagating virus in the cell culture, adding a nuclease enzyme to the cell culture shortly before the end of virus propagation to digest nucleic acid material released from the lysing host cells into the medium, harvesting the virus and obtaining viral antigens thereof by extraction in order to make the viral antigen vaccine. The patent is silent with regard to the kind of nutrient medium used for virus propagation and also with regard to the addition of a protease, usually required for the final processing of influenza virus hemagglutinin to get infectious virus. The method further requires various purification steps for providing a ready-for-use vaccine preparation.

It is known, however, that the nature the host substrate as well as the composition of the nutrient medium used for virus propagation may significantly affect immunogenicity and antigenicity of the virus progeny obtained therewith. Particularly, serum-containing media may not only decrease antigenicity of viral progeny but additionally may decrease protease activity in the medium, hence inhibit virus maturation, and subsequently require expensive steps of purification.

SUMMARY OF THE INVENTION

The present invention overcomes the drawbacks of the prior art. It relates to a simple and efficient process for isolating viruses from various sources and for producing viral progeny for use as vaccines, particularly live attenuated influenza vaccines, in under conditions where alterations in the surface antigens of the virus due to adaptive selection are minimized or entirely prevented.

It is also an object of the present invention to provide for a method for the production of viruses, particularly influenza viruses, that yields viral progeny that selectively agglutinates human erythrocytes but not chicken erythrocytes, and that preferably has antigenic properties identical with those of the initially inoculated virus strain, e.g. a primary clinical wild-type isolate.

In a preferred embodiment, the nucleic acid sequence of the HA gene and optionally of the NA gene of the propagated virus is identical with the one of the initially inoculated strain (e.g. an epidemic strain, primary clinical isolate of an infected patient).

It is another object of the invention to provide a method for efficient production of a whole-virus vaccine, particularly a live attenuated vaccine, in a single step procedure that does not require any chromatographic or other purification steps of the virus suspension harvested from the cell culture supernatant by centrifugation, particularly no protein separation or purification steps.

It is yet another object of the invention to provide attenuated, cold adapted and temperature sensitive influenza A and B strains and vaccines made thereof.

DETAILED DESCRIPTION OF THE INVENTION

Figure 1:
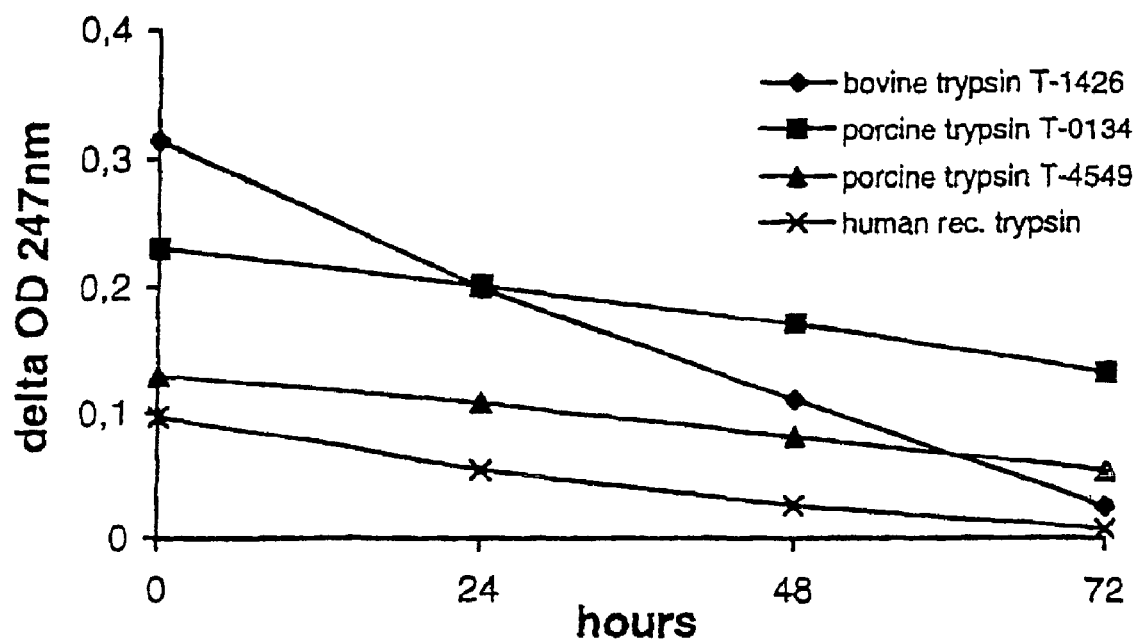
FIG. 1 is a graphic illustration of the time course of trypsin inactivation in the supernatant of a Vero cell culture.

Comparative experiments using embryonated eggs, MDCK and Vero cells clearly proved that the initially inoculated virus is likely to undergoe antigenic alteration during growth on any one of these substrates Our experiments confirmed that the alterations are least or even absent for influenza virus strains grown on Vero cells in serum-free medium. Moreover, it turned out that influenza A viruses, at least strains of the H3N2 subtype, when multiplied on Vero cells in serum-free and protein-free medium exhibit a selectivity for agglutination of human erythrocytes but not for chicken erythrocytes. Also, they did not grow on eggs. This was a first indication that these Vero-grown viruses might be more identical with the wildtype virus of the corresponding clinical isolate than the ones grown on MDCK cells or eggs.

Indeed, comparison of the HA and NA gene sequences of wildtype isolates obtained from nasal swabs with the ones of the same viruses after growth on Vero and MDCK cells, respectively, revealed alterations in the HA or NA of MDCK-grown viruses relative to the HA or NA of the swab isolates or of the Vero-grown viruses or of both the swab isolates and the Vero-grown viruses.

Moreover, experimental data obtained from immunizations of ferrets with Vero- and MDCK-grown wildtype viruses indicate a far stronger virulence of the Vero-grown viruses compared to the MDCK-grown viruses. Also, the immunogenicity of the Vero-grown viruses tested in an animal trial on macaques was demonstrated to be significantly superior to the one of the viruses grown on MDCK cells or eggs.

These findings together provide strong evidence for the hypothesis that the process for the multiplication and propagation of viruses according to the present invention as hereinafter described in more detail yields viruses that are either unaltered compared to the initially inoculated (e.g. wildtype) virus or are modified to only a minor extent.

It is not only the avoidance of antigenic alterations that makes the present process of virus multiplication so unique, but it is also its striking simplicity which makes it extremely suitable for large scale industrial vaccine production.

Further experiments have shown that the source of trypsin (or trypsinogen) may be one additional factor that influences the overall yield of infective virions. Indeed, while the methods known in the art (e.g, Kaverin and Webster, J Virol 69/4: 2700-2703, 1995; or U.S. Pat. No. 5,753,489) use either repeated addition of trypsin (Kaverin and Webster) or high trypsin concentrations (U.S. Pat. No. 5,753,489), the process according to the present invention applies only half or less of the trypsin concentrations reported in the prior art. Moreover, a single addition of as little as 0.5-10 µg, preferably 2-5 µg trypsin per ml to the cell culture medium prior to or at the beginning of incubation of the infected host cells is sufficient to reach optimal infective virus titers. Inactivation experiments revealed that porcine or human recombinant trypsins are far less susceptible to inactivation by Vero or MDCK cells than bovine trypsin. Since bovine trypsin is most commonly used in the art it is rather likely that prior art literature unless explicitly mentioning another trypsin source, implicitly refers to bovine trypsin only. This would also help to explain the modes and concentrations of trypsin application recited, for instance, in Kaverin et al. and in U.S. Pat. No. 5,753,489.

Using porcine or human rec trypsin or trypsinogen for initially supplementing the serum-free medium for Vero cell cultures according to the present invention therefore allows to use extremely low trypsin or trypsinogen concentrations and thus prevents the need of labor-intensive and costly purification steps after harvesting of the virus-containing supernatant.

Another step that contributes to make the present process simple and therefore attractive to vaccine manufacturers is the addition of a single dose of highly active endonuclease to the cell culture medium prior to or at the beginning of incubation of the infected Vero cells for virus propagation. This endonuclease, preferably Benzonase™, is added once to the medium at a very low initial concentration of 2-30, preferably 5-15, Units per ml of medium and effectively clears the cell culture medium from free DNA and RNA originating mainly from the lysing or lysed host cells. The residual Benzonase enzyme concentration in the ready-for-use vaccine preparations obtained from the centrifuged supernatant remains at 5 ng or less per dose.

Benzonase™ is a trademark of Nycomed Pharma A/S Denmark and relates to an extracellular unspecific endonuciease obtained from *Serratia marcescens*. Benzonase is a genetically engineered endonuclease which degrades both DNA and RNA strands in many forms to small oligonucleotides. It promotes quick reduction of the viscosity of cell lysates, which facilitates ultracentrifugation. It reduces proteolysis and increases the yield in targeted protein and offers complete elimination of nucleic acids from, e.g. recombinant, proteins. It has an exceptionally high activity of 400,000 U/mg.

A third and important advantage of the present process is the factor time hence process costs. Due to the use of serum-free medium that does not contain proteins of animal origin and preferably no antibiotics, expensive and time-consuming purification procedures can be reduced to a minimum or even totally avoided. Also, because the addition of exogenous enzymes such as the protease (e.g. trypsin or trypsinogen) and nuclease (e.g. Benzonase) occurs once at the beginning of the virus propagation phase this saves plenty of time that the state-of-the-art methods require for post-incubation treatment of the virus-containing culture supernatant (e.g., HA activation, RNA/DNA digestion, protein purification, etc.).

Surprisingly, it turned out that the early addition of either or both of protease (e.g. trypsin or trypsinogen) and nuclease (e.g.Benzonase) to the virus-infected Vero-cell culture had no negative implications on the virus yield, which is probably due to the very low enzyme concentrations applicable in the process of the present invention.

The present process of virus propagation is useful for the multiplication of various kinds of viruses, particularly influenza A viruses of the H3N2 subtype, but is also suitable for the isolation and reproduction of any epidemic or laboratory influenza virus strain, regardless of the kind of virus inoculum (e.g., blood serum sample, nasal wash, nasal swab, pharyngeal swab, saliva, etc.). Using the principles of this process, a number of influenza A and B vaccines has been produced which are part of the present invention and which are characterized in more detail in the subsequent Examples.

Also, protective efficacy as well as vaccine safety have been confirmed for the vaccines made according to the present invention, as will be demonstrated in the Examples.

The term "protein-free" or "free of non-serum proteins" as used herein in connection with the method of virus multiplication or propagation according to the present invention shall mean free of any functionally active protein. It shall not exclude, however, non-functional peptides as may originate from protein hydrolysates such as yeast extract or soya extract. Unless stated otherwise, the term "protein-free"0 shall neither exclude the presence of a protease and a nuclease enzyme at the concentrations disclosed and claimed herein.

In a preferred embodiment, the present invention relates to a simple, reliable and highly economic method for the manufacture of a whole-virus vaccine, preferably of an attenuated live vaccine, comprising the steps of:
a) infecting African Green Monkey Kidney (Vero) cells with a desired virus, wherein the Vero cells have been grown in and separated from a serum-free medium that is also free of non-serum proteins;
b) combining the infected cells with a suitable serum-free cell culture medium that is also free of non-serum proteins except for a protease and a nuclease; and
c) incubating the cells in the presence of said protease and said nuclease to allow for production of infectious virus and, simultaneously, for digestion of nucleic acid material released to the cell culture medium;
d) harvesting infectious virus by collecting virus-containing supernatant obtained from centrifugation of the cell culture; and
e) preparing a vaccine thereof comprising subjecting the virus-containing supernatant to at least one processing step selected from the group consisting of filtering, concentrating, freezing, freeze-drying, and stabilizing by addition of a stabilizing agent.

It is preferred that the virus used for propagation has never had any contact to a host substrate other than a Vero cell line. This will ensure best results with regard to immunogenic and antigenic identity of the initial virus (e.g. nasal swab isolate) and the viral progeny obtained after propagation.

It is also preferred that the virus used for propagation, particularly for the manufacture of a whole-virus vaccine, preferably an influenza attenuated live vaccine, is an influenza virus selected from the group consisting of strains A/Sing/1/57ca, A/Sing/1/57ca/ΔNS 87, A/Sing/1/57ca/ΔNSPR8, A/Sing/1/57ca/NS124PR8, B/Vienna/1/99ca, B/Vienna/99/ca37 and any attenuated variants and reassortants derived from any one of these strains. The genetic characteristics of the preferred virus strains, e.g. master strains, are disclosed in full detail in the subsequent Examples.

Influenza strains A/Sing/1/57ca, A/Sing/1/57ca/ΔNS87, A/Sing/1/57ca/ΔNSPR8, A/Sing/1/57ca/ΔNS 124PR8, B/Vienna/1/99/22ca, and B/Vienna/1/99/37ca were deposited at the National Bank of Industrial Microorganisms and Cell Cultures located at 1113 Sofia, 125 Tsarigradsko chausse blvd., bl. 2, P.O. Box 239, Bulgaria on May 9, 2006. The deposit of A/Sing/1/57ca, with a scientific description, was assigned NBIMCC Number 8460. The deposit of A/Sing/1/57ca/ΔNS87, with a scientific description, was assigned NBIMCC Number 8461. The deposit of A/Sing/1/57ca/ΔNSPR8, with a scientific description, was assigned NBIMCC Number 8462. The deposit of A/Sing/1/57ca/ΔNS124PR8, with a scientific description, was assigned NBIMCC Number 8463. The deposit of B/Vienna/1/99/22ca, with a scientific description, was assigned NBIMCC Number 8464. The deposit of B/Vienna/1/99/37ca, with a scientific description, was assigned NBIMCC Number 8465.

In another embodiment, the present invention refers to a whole-virus vaccine itself, preferably to an attenuated live vaccine, which in its ready-for-use form comprises essentially unmodified, optionally filtered and/or concentrated, virus-containing supernatant of a serum-free and protein-free Vero cell culture used for production of said virus. It is particularly preferred that the vaccine is produced according to the method of the present invention as disclosed and claimed herein.

This "one-step" vaccine, which does not require further processing, e.g., purification steps other than centrifugation and/or conventional filtration (i.e. not gel filtration), is compliant with the requirements for FDA approval.

The term "essentially unmodified" as used herein with regard to virus-containing supernatant in vaccine preparations according to the present invention shall refer to the composition of the supernatant as is at the time of harvesting the propagated virus, i.e. to the composition of the soluble components and ingredients present in the liquid phase of the supernatant. Minor alterations of the composition of ingredients as may occur due to steps of, for example, filtration, sterile filtration, centrifugation, concentration, drying, or freeze-drying of the virus-containing supernatant, shall be regarded as falling within the scope of "essentially unmodified". Also, the term shall not exclude the presence of preserving and/or stabilizing agents usually applied in the art to vaccine preparations.

The whole-virus vaccines of the present invention may be used for the prophylactic or therapeutic treatment of viral infections, particularly of influenza virus infections. They may be administered as known in the art, e.g. intravenously, subcutaneously, intramuscularly or, most preferably, intranasally. The virus strains disclosed herein and the vaccines made thereof may, however, also be used as vectors or shuttles to present heterologous antigens to the immune system, e.g. antigens of viral envelope proteins such HIV-1 or hepatitis antigens.

Further preferred embodiments are defined in the dependent claims.

In order that the invention described herein may be more fully understood, the following Examples are set forth. They are for illustrative purposes only and are not to be construed as limiting this invention in any respect.

EXAMPLE 1

Virus Production

Cultivation of Vero/SF (=serum-free) cells:

SF-Medium: DMEM (Biochrom F0435), Ham's F12 (Biochrom F0815), 5 mM L-Gln, 0.1% SF-supplement (a) or (b); antibiotics (only for first passage of virus isolation).

SF-Supplement: protein hydrolysate of non-animal origin, without functional proteins such as insulin, transferrin or growth factors:

a) 62.5 g hy-soy/UF, Quest 5X59100, to 500 g HQ-water, filtered with PES 0.2 μm filter;
b) 12.5 g hy-pep 1510, Quest, to 100 g HQ-water, filtered with PES 0.2 μm filter.

The content of a deep frozen (liquid nitrogen) disinfected (70% ethanol) ampule of WCB Vero cells was thawed and added to 9 ml of cold serum-free (SF) medium in a 10 ml tube and centrifuged for 10 min at 1000 rpm (170 g). The pellet was resuspended in SF-medium to a total of 30 ml, transferred to a 80 $cm^2$ Roux bottle and incubated at 37° C. and 7% $CO_2$ for at least 15 min. Thereafter, the medium was removed and the cells were washed with approx. 0.1 ml/$cm^2$ PBS def. (=PBS without $Ca^{2+}$ and $Mg^{2+}$). Addition of trypsin/EDTA-solution (8-10 μl/$cm^2$; 0.1% trypsin/0.02% EDTA-solution) and incubation at room temperature for about 3 min. Detaching by gently pushing the Roux bottle against palm of the hand, addition of SF-medium and trypsin inhibitor (Sigma, T6522) at a quantity of about ⅕ of volume of the trypsin/EDTA solution. Repartition of the cell suspension to Roux bottles or roller bottles, incubation at 37° C. and 9% $CO_2$.

MDCK cells were grown in DMEM/Ham's F12+2% FCS (heat inactivated); embryonated hen eggs were 11-12 days old and of SPF (specific pathogen free) origin.

Propagation of Virus Strains:

Old medium from roller bottles containing Vero cells was removed and cells were infected with virus by addition of 5 ml virus suspension in SF-medium to each roller bottle, resulting in an MOI (multiplicity of infection) of approximately 0.01. After incubation for 45 minutes at 33° C. the virus inoculum was removed with a pipette. 90 ml of SF-medium supplemented with 0.5-10, preferably 2-5 and most preferably 2 µg/ml porcine trypsin (supplier: AvP) or human recombinant trypsin or trypsinogen (own production) and 0.5 g/l sodium bicarbonate were added to each roller bottle and the bottles incubated at 33° C. and 5% $CO_2$. For the production of attenuated live vaccine samples for use in animal testing and in human clinical trials the SF-medium was supplemented with trypsin and, additionally, with Benzonase™ at a concentration of 2-30, preferably 5-15, and most preferably 10 Units of Benzonase™ per ml of medium. Virus was harvested after 64 hours post infection by centrifugation of the culture supernatant for 5 min at 4000 rpm (3000 g) at 10° C. in 50 ml-tubes. The supernatant was pooled for each virus strain and stored at +4° C. Aliquots thereof were used for vaccine testing.

For storage purposes the virus preparations may be freeze-dried and stabilizer such as, for example, trehalose and lactalbumin enzymatic hydrolysate in HEPES buffer may be added. Reconstitution may be done with sterile water.

EXAMPLE 2

Comparison of Trypsin Inactivation in Cell Cultures

TABLE 1

Trypsin inactivation in Vero vs. MDCK cell culture

| | Vero/MDCK | | | |
|---|---|---|---|---|
| | 0 h | 24 h | 48 h | 72 h |
| bovine trypsin | 0.314/0.314 | 0.199/0.239 | 0.110/0.201 | 0.026/0.203 |
| porcine trypsin (high) | 0.230/0.230 | 0.201/0.206 | 0.171/0.209 | 0.133/0.201 |
| porcine trypsin (low) | 0.129/0.129 | 0.108/0.118 | 0.081/0.099 | 0.054/0.116 |
| human rec trypsin | 0.097/0.097 | 0.054/0.088 | 0.026/0.080 | 0.008/0.076 |

Figure 2:
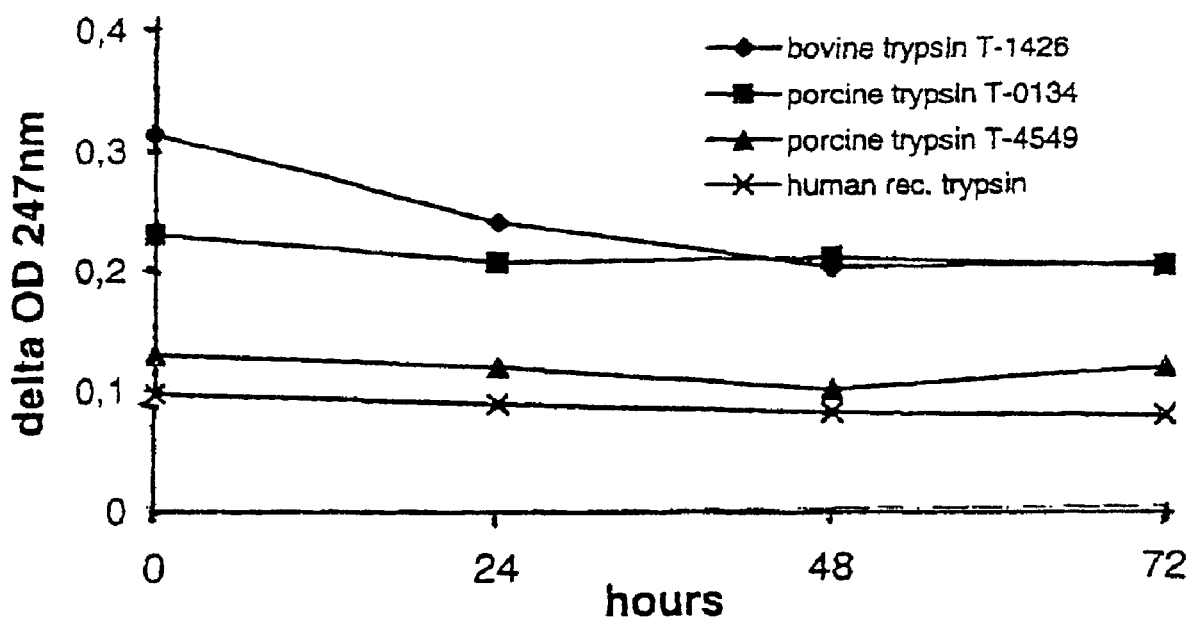
FIG. 2 is a graphic illustration of the time course of trypsin inactivation in the supernatant of a MDCK cell culture.

Supernatants obtained from uninfected Vero cell cultures (grown in SF medium as described in Example 1) and MDCK cell cultures (grown in FCS-supplemented medium as described in Example 1) were tested for their capacity to inactivate trypsin of different origin that has been added to the supernatant at time =0 h at equal concentrations each. Porcine trypsin has been applied in two different qualities (obtained from different manufacturers), i.e. with high or low activity. The results are presented in Table 1 and in FIGS. 1 and 2.

The data unambiguously show that bovine trypsin is rapidly inactivated in Vero cell culture supernatant and less rapidly in MDCK cell culture supernatant. Porcine and human rec trypsin (manufactured in our laboratories) remain fully active in MDCK supernatants while they are gradually inactivated in Vero supernatants at approximately half or less of the velocity of bovine trypsin inactivation. The difference of the porcine trypsins tested is only in the starting OD-level at 247 nm, while the inactivation characteristics are essentially identical for both lots of porcine trypsin.

EXAMPLE 3

Comparison of Various Viral Properties After Growth on Different Host Cell Substrates Virus propagation was carried out as described in Example 1 for the different host cell substrates. Each of the seven isolates recovered on Vero cells was reactive with human erythrocytes but not with chicken erythrocytes and none of them accumulated in embryonated eggs. On the other hand, all isolates recovered on MDCK cells were reactive both with chicken and human erythrocytes and were capable of growing in eggs. Although these differences were not seen in influenza A viruses of the H1N1 substype nor in influenza B isolates (see subsequent Tables 3 and 4), it may nevertheless be assumed that cultivation of influenza viruses on Vero cells will maintain antigenic properties more properly than cultivation on other substrates.

TABLE 2

Characteristics of H3N2 viruses isolated from clinical material on Vero/SF cells

| | | | HA titer with | | |
|---|---|---|---|---|---|
| Isolate number | Antigenically related to | Isolated on | chicken erys | human erys | Growth in eggs |
| A/47/96 | A/Johannesburg/33/94 | Vero | − | + | − |
| | | MDCK | + | + | + |
| A/7729/98 | A/Sydney/5/97 | Vero | − | + | − |
| | | MDCK | + | + | + |
| A/1143/99 | A/Sydney/5/97 | Vero | − | + | − |
| | | MDCK | + | + | + |
| A/1144/99 | A/Sydney/5/97 | Vero | − | + | − |
| | | MDCK | + | + | + |
| A/1179/99 | A/Sydney/5/97 | Vero | − | + | − |
| | | MDCK | + | + | + |
| A/1180/99 | A/Sydney/5/97 | Vero | − | + | − |
| | | MDCK | + | + | + |
| A/1182/99 | A/Sydney/5/97 | Vero | − | + | − |
| | | MDCK | + | + | + |

From the data in Table 3 it appears that H1N1 influenza viruses may be less susceptible to adaptive selection, as the Vero and MDCK-grown isolates do not exhibit significant differences in their hemagglutination characteristics nor in their HA sequences. A similar conclusion may be drawn for the B isolates listed in Table 4.

The clinical starting material (e.g. serum samples, swabs) for virus isolation and replication was primarily obtained from:

1. Institute of Virology, Vienna, Austria (Prof. F. Heinz) 1995/96, 1996/97
2. Unité de Génétique Moléculaire des Virus Respiratoires, Institute Pasteur, Paris, France (Prof. S. van der Werf) 1996/97
3. Public Health Laboratory Service, London, UK (Dr. M. Zambon) 1996/97
4. Laboratoire Central de Virologie, Hôpitaux Universitaires de Genéve, Geneva, Switzerland (Dr. W. Wunderli) 1996/97, 1997/98
5. Virus Unit, Queen Mary Hospital, Hong Kong (Dr. W. L. Lim) 1997/98

TABLE 3

Characteristics of H1N1 viruses isolated from clinical material on Vero/SF cells

| Isolate number | Antigenically related to | Isolated on | HA titer with chicken erys | human erys | Growth in eggs | Changes in HA1 at position 225 |
|---|---|---|---|---|---|---|
| A/5389/95 | A/Bayern/7/95 | Vero | + | + | + | D |
|  |  | MDCK | + | + | + | D |
| A/1035/98 | A/Beijing/262/95 | Vero | + | + | + | D |
|  |  | MDCK | + | + | + | D |
|  |  | Egg | + | + | + | G |
|  |  | Swab |  |  |  | D |
| A/1131/98 | A/Beijing/262/95 | Vero | + | + | + | D |
|  |  | MDCK | + | + | + | D |
|  |  | Swab |  |  |  | D |
| A/1134/98 | A/Beijing/262/95 | Vero | + | + | + | D |
|  |  | MDCK | + | + | + | D |
|  |  | Egg | + | + | + | n.t. |
|  |  | Swab |  |  |  | D |

TABLE 4

Characteristics of B viruses isolated from clinical material on Vero/SF cells

| Isolate number | Antigenically related to | Isolated on | HA titer with chicken erys | human erys | Growth in eggs | Changes in HA1 at position 198 |
|---|---|---|---|---|---|---|
| B/4291/97 | B/Beijing/184/93 | Vero | + | + | + | identical |
|  |  | MDCK | + | + | + |  |
| B/1/99 | B/Beijing/184/93 | Vero | + | + | + | T(g.s) |
|  |  | MDCK | + | + | + | T(g.s) |
|  |  | EGG | + | + | + | A |
|  |  | Swab |  |  |  | T(g.s) |
| B/110/99 | n.t. | Vero | + | + | + | identical |
|  |  | MDCK | + | + | + |  |
| B/147/99 | n.t. | Vero | + | + | + | identical |
|  |  | MDCK | + | + | + |  |
| B/156/99 | B/Beijing/184/93 | Vero | + | + | + | identical |
|  |  | MDCK | + | + | + |  |
| B/157/99 | B/Beijing/184/93 | Vero | + | + | + | identical |
|  |  | MDCK | + | + | + |  |

TABLE 5

Amino acid changes in HA, NA and M proteins of H3N2 influenza viruses isolated on different host systems

| | Changes at positions | | | | | | | | |
|---|---|---|---|---|---|---|---|---|---|
| | HA | | | | | | NA | | |
| Isolate number | 128 | 129 | 229 | 133 | 218 | 220 | 136 | 151 | M |
| A/47/96 Vero | T(g.s) | | | | | | | | |
| A/47/96 MDCK | A | | | | | | | | |
| A/7729/98 Vero | | E | R | | | | | | |
| A/7729/98 MDCK | | G | K | | | | | | |
| A/1143/99 Swab | | | | N(g.s) | G | | n.t | n.t | n.t |
| A/1143/99 Vero | | | | N(g.s) | G | | | D | identical |
| A/1143/99 MDCK | | | | D | E | | | G | |
| A/1144/99 Swab | | | | | | R | n.t | n.t | n.t |
| A/1144/99 Vero | | | | | | R | | identical | identical |
| A/1144/99 MDCK | | | | | | G | | | |
| A/1179/99 Swab | | | identical | | | | n.t | n.t | |
| A/1179/99 Vero | | | | | | | | identical | identical |
| A/1179/99 MDCK | | | | | | | | | |

TABLE 5-continued

Amino acid changes in HA, NA and M proteins of H3N2 influenza viruses isolated on different host systems

| | Changes at positions | | | | | | | | |
|---|---|---|---|---|---|---|---|---|---|
| | HA | | | | | | NA | | |
| Isolate number | 128 | 129 | 229 | 133 | 218 | 220 | 136 | 151 | M |
| A/1180/99 Swab | | | identical | | | | n.t | n.t | n.t |
| A/1180/99 Vero | | | | | | | Q | | identical |
| A/1180/99 MDCK | | | | | | | R | | |
| A/1182/99 Swab | | | identical | | | | n.t | | n.t |
| A/1182/99 Vero | | | | | | | n.t | | n.t |
| A/1182/99 MDCK | | | | | | | n.t | | n.t |

The results show that with some isolates there was no alteration of the HA sequence of Vero or MDCK propagated viruses over the HA sequence directly obtained from the swab material by PCR amplification. In some other isolates grown on MDCK cells the HA and/or NA sequences were deviating from the corresponding sequences obtained on Vero cells. The Vero-derived viruses did not show, however, any deviations in the HA sequence over the HA sequence of the swab isolates, where determined.

TABLE 6

Immunogenicity of Vero-, MDCK- and Egg-derived viruses for macaques

| Animal number | Virus for immunization | Dose, PFU/ml | Serum HI titers |
|---|---|---|---|
| 96 | A/Vienna/47/96 V | $5 \times 10^4$ | 256 |
| 88 | A/Vienna/47/96 V | $5 \times 10^4$ | 128 |
| 15 | A/Vienna/47/96 V | $1.0 \times 10^6$ | 128 |
| 95 | A/Vienna/47/96 V | $1.0 \times 10^6$ | 256 |
| 93 | A/Vienna/47/96 M | $1.0 \times 10^6$ | 16 |
| 128 | A/Johannesburg/33/94 E | $5 \times 10^6$ | 32 |
| 110 | A/Vienna/157/97 V | $5 \times 10^4$ | 128 |
| 78 | A/Wuhan/359/95 E | $5 \times 10^6$ | 32 |

The Macaques were immunized i.n. in the absence of anesthesia with 1 ml of virus suspension
V—Vero- isolated virus
M—MDCK- isolated viruses
E—egg isolated viruses

TABLE 7

Virulence of Vero- and MDCK- derived variants of A/Vienna/47/96 wt virus for ferrets

| | Virus dose, | Number of animals with fever on day | | |
|---|---|---|---|---|
| Viruses | PFU/ml | 1 | 2 | 3 |
| A/Vienna/47/96 Vero | $2 \times 10^2$ | FF | FFF | |
| | $1 \times 10^3$ | FFF | FFF | |
| A/Vienna/47/96 MDCK | $5 \times 10^2$ | | | |
| | $5 \times 10^3$ | | FF | |
| | $5 \times 10^4$ | FF | F | F |

Animals were immunized i.n. under ether narcosis with 1 ml of virus suspension.
N—normal temperature from 38.1° C. to 39.9° C.;
F—fever, more than 40.0° C.

The most surprising, yet important result in Table 6 is the very low immunogenicity of MDCK-derived A/Vienna/47/96 virus compared with the corresponding Vero-derived virus. It is no particular surprise that the egg-derived viruses show only poor immunogenicity.

Similarly, the results listed in Table 7 indicate that Vero-derived viruses are less, if at all, altered by adaptive selection on their host substrate in comparison to MDCK-derived viruses. This means that relative to the MDCK-derived viruses the Vero-derived viruses maintain more or even all of the immunologically relevant, particularly antigenic, properties of the original virus.

EXAMPLE 4

Vaccine Production with Preferred Strains

The process described in Example 1 was also used for the production of vaccine samples for animal testing and human clinical studies. It is understood that the process of virus propagation described therein also encompasses variations that could be suggested or applied by a person of ordinary skills in the art without inventive input and as long as the variations do not change the sense of the present invention as described herein and in the claims.

Vaccine samples containing one or more of the preferred influenza A or B wildtype strains, master strains or reassortant strains (that are subsequently described in more detail) were exclusively produced using the continuous Vero cell line as the host cell system (unless for purposes of comparison with samples obtained from other host substrates) in serum-free medium additionally supplemented with the nutritional ingredients and enzymes as described in Example 1.

Some methods suitable for modifying wildtype viruses including the methods of attenuation (e.g., temperature sensitivity), cold adaptation and reassortment are known in the art and extensively reviewed, for instance, in WO 99/64068.

Further characteristics of the two most preferred influenza A and B master strain candidates useful for attenuated live vaccine production, e.g., by 6/2 reassortment with the HA and NA genes of actual epidemic influenza viruses recommended by the WHO, are given in the following Tables 8-13.

TABLE 8

Characteristics of master strain candidates for live influenza vaccines

|  | Influenza A A/Singapore/1/57/ca H2N2 | Influenza B B/Vienna/1/99/ca |
|---|---|---|
| Passage history | A/Singapore/1/57 wt egg derived H2N2 20 passages at 37° C. on Vero/SF cells 25 passages at 25° C. on Vero/SF cells | B/Vienna/1/99 wt Vero derived 1 additional passage at 33° C. on Vero/SF cells 22 passages at 25° C. on Vero/SF cells |
| Method of attenuation | Serial passages at optimal and suboptimal temperature on heterologous system | Serial passages at optimal and suboptimal temperature on heterologous system |
| Phenotypic markers | temperature sensitive (ts) cold adapted (ca) very low reproduction in mouse lungs | temperature sensitive (ts) cold adapted (ca) very low reproduction in mouse lungs |
| Genotypic markers | Mutations: 13 (8 coding) PB2 3 (2 coding) PB1 2 (1 coding) PA 4 (3 coding) NP 1 M 2 (2 coding) NS 1 | Mutations: 5 (3 coding) PB2 0 PB1 1 PA 0 NP 2 (1 coding) M 1 NS 1 |

TABLE 9

Full Sequence of the 8 genome segments and of the 10 corresponding proteins of strain A/Singapore/1/57/ca A/Singapore/1/57/ca (H2N2)

| RNA segment | Nucleotide sequence (cDNA) | Protein | Amino acid sequence |
|---|---|---|---|
| 1 | SEQ ID No. 1 | PB2 | SEQ ID No. 9 |
| 2 | SEQ ID No. 2 | PB1 | SEQ ID No. 10 |
| 3 | SEQ ID No. 3 | PA | SEQ ID No. 11 |
| 4 | SEQ ID No. 4 | HA | SEQ ID No. 12 |
| 5 | SEQ ID No. 5 | NP | SEQ ID No. 13 |
| 6 | SEQ ID No. 6 | NA | SEQ ID No. 14 |
| 7 | SEQ ID No. 7 | M1 | SEQ ID No. 15 |
|  |  | M2 | SEQ ID No. 16 |
| 8 | SEQ ID No. 8 | NS1 | SEQ ID No. 17 |
|  |  | NS2 | SEQ ID No. 18 | ca—cold adapted

It shall be noted, however, that the genome segments No. 4 and 6, i.e., the HA and NA genes, are not required to characterize the influenza A master strain candidates, because these genes will be exchanged for the corresponding genes of actual epidemic influenza viruses (as mentioned hereinbefore). The features important for the safety of a vaccine, e.g. temperature sensitivity, or features that allow intranasal administration of a vaccine, namely cold adaptation (because the average temperature in a nose is lower than the usual body temperature), are primarily caused by mutations in the remaining 6 genome segments.

The following Table 10 lists the mutations in the genome segments of A/Singapore/1/57/ca compared to the corresponding wildtype strain A/Singapore/1/57/wt.

TABLE 10

Mutations in the genome segments of attenuated, temperature sensitive, cold adapted influenza strain A/Singapore/1/57/ca compared to A/Singapore/1/57/wt strain

| RNA seg-ment | Length (n"ds) | Nucleotides changed position | wt | ca | Protein | Length (aa) | Amino acids changed position | wt | ca |
|---|---|---|---|---|---|---|---|---|---|
| 1 | 2341 | 252 | a | g | PB2 | 771 | — | — | — |
|  |  | 581* | t | c |  |  | 185 | I | T |
|  |  | 1046* | g | t |  |  | 340 | R | I |
| 2 | 2341 | 1279* | t | a | PB1 | 757 | 419 | L | I |
|  |  | 1965 | a | c |  |  | — | — | — |
| 3 | 2233 | 707* | a | t | PA | 716 | 228 | I | N |
|  |  | 1425 | t | a |  |  | — | — | — |
|  |  | 1537* | a | g |  |  | 505 | V | I |
|  |  | 1819* | g | c |  |  | 598 | Q | E |
| 5 | 1565 | 210 | g | a | NP | 506 | — | — | — |
| 7 | 1027 | 327* | g | a | M1 | 252 | 101 | R | K |
|  |  | 499* | g | c |  |  | 158 | Q | R |
|  |  |  |  |  | M2 | 97 | — | — | — |
| 8 | 890 | 813 | a | g | NS1 | 237 | — | — | — |
|  |  |  |  |  | NS2 | 121 | — | — | — |

Total number of mutations - 13 (8 coding)
*coding mutations

Preferred variants of A/Sing1/57/ca comprise the ones listed in the following Table 11, wherein "Δ" means "del" or "delta" and stands for a mutant that contains at least one "deletion" in its NS gene segment.

TABLE 11

Preferred variants of A/Sing/1/57/ca

|  | A/Sing/1/57/ca | Sing ca/ΔNS 87 | Sing ca/ΔNSPR8 | Sing ca/NS124PR8 |
|---|---|---|---|---|
| PB2 (Sing ca*) | ○●● | ○●● | ○●● | ○●● |
| PB1 (Sing ca*) | ●○ | ●○ | ●○ | ●○ |
| PA (Sing ca*) | ●○●● | ●○●● | ●○●● | ●○●● |
| HA |  |  |  |  |
| NP (Sing ca*) | ● | ● | ● | ● |
| NA |  |  |  |  |

TABLE 11-continued

Preferred variants of A/Sing/1/57/ca

|  | A/Sing/1/57/ca | Sing ca/ΔNS 87 | Sing ca/ΔNSPR8 | Sing ca/NS124PR8 |
|---|---|---|---|---|
| M1, 2 (Sing ca*) | ●●○ | ●●○ | ●●○ | ●●○ |
| NS1, 2 (Sing ca*) | ○ | ■ ○ del 87 aa NS1 | | |
| NS1, 2 (PR8**) | | | ▨■▨ del NS1 | ▨●▨ Stop 124 NS1 |

Phenotypes

| | | | | |
|---|---|---|---|---|
| ca | + | + | + | + |
| ts | + | + | + | + |
| IFN-induct. | − | +/− | + | + |
| IFN-sensit | − | + | + | − |

*genome segment originating from A/Singapore/1/57/ca
**genome segment originating from influnza A/PR8/34
ca—cold adapted; ts—temperature sensitive; aa—amino acid(s)
IFN-induct.—strain causes interferon release in host substrates that are able of IFN production, as well as in animal or human immune systems upon administration.
IFN-sensit.—strain is sensitive towards interferon; replication in IFN producing systems is reduced or stopped.
Sing ca/ΔNS 87—strain A/Singapore/1/57/ca containing deletion of 87 amino acids in NS1 gene at aa position 36-123.
Sing ca/ΔNSPR8—strain A/Singapore/1/57/ca containing the NS gene segment from A/PR8/34 (herein also abbreviated "PR8") which contains a deletion of the entire NS1 gene.
Sing ca/NS124PR8—strain A/Singapore/1/57/ca containing the NS gene segment from A/PR8/34 which contains a stop codon at aa position 124 of the NS1 gene.
+/− means that the phenotype needs further clarification and can not yet be unambiguously defined.

The following Tables 12, 13 and 13A refer to preferred influenza B master strain candidates and to variations and reassortants, respectively, thereof.

TABLE 12

Full Sequence of the 8 genome segments and of the 11 corresponding proteins of strain B/Vienna/1/99/ca B/Vienna/1/99/ca

| RNA segment | Nucleotide sequence (cDNA) | Protein | Amino acid sequence |
|---|---|---|---|
| 1 | SEQ ID No. 19 | PB2 | SEQ ID No. 27 |
| 2 | SEQ ID No. 20 | PB1 | SEQ ID No. 28 |
| 3 | SEQ ID No. 21 | PA | SEQ ID No. 29 |
| 4 | SEQ ID No. 22 | HA$_0$ | SEQ ID No. 30 |
| 5 | SEQ ID No. 23 | NP | SEQ ID No. 31 |
| 6 | SEQ ID No. 24 | NB | SEQ ID No. 32 |
| | | NA | SEQ ID No. 33 |
| 7 | SEQ ID No. 25 | M1 | SEQ ID No. 34 |
| | | BM2 | SEQ ID No. 35 |
| 8 | SEQ ID No. 26 | NS1 | SEQ ID No. 36 |
| | | NS2 | SEQ ID No. 37 | ca—cold adapted

The original strain B/Vienna/1/99 was isolated on Vero cell culture grown with serum-free medium in February 1999 in Vienna, Austria from a 12 year old female with acute influenza. It was rated as B/Beijing/184/93-like by the Center for Disease Control (CDC), Atlanta, USA. After an additional passage at 33° C. the wildtype strain—designated as B/Vienna/1/99 wt—was attenuated by 22 serial passages at 25° C. using the same cell culture system. The plaque purification was done at 25° C. for the first and at 33° C. for the following four rounds. The derived plaque purified clone was amplified and stored at −70° C., designated as B/Vienna/1/99 ca or briefly BV22. The identity as a B/Beijing/184/93-like virus was confirmed by HI-assay with standard anti-serum from NIBSC.

TABLE 13

Mutations in B/Vienna/1/99/ca (=BV22) compared to B/Vienna/1/99/wt (BVie) 1. passage on Vero/SF

| Segment (lenght in nucleotides) | Nucleotides changed | | | Protein (length in amino acids) | Amino acids changed | | |
|---|---|---|---|---|---|---|---|
| | Position | BVie | BV22 | | Position | BVie | BV22 |
| 1 (2396) | — | — | — | PB2 (770) | — | — | — |
| 2 (2369) | 594 | T | C | PB1 (752) | — | — | — |
| 3 (2305) | — | — | — | PA (726) | — | — | — |
| 4 (1882) | 457 | G | A | HA$_0$ (584) | 142 | A | T |
| | 1299 | G | T | | 422 | K | N |
| | 1595 | G | A | | 521 | G | E |
| 5 (1844) | 128 | C | T | NP (560) | 23 | S | F |
| | 330 | T | C | | — | — | — |
| 6 (1557) | — | — | — | NB (100) | — | — | — |
| | 823 | G | A | NA (466) | 257 | R | Q |
| | 1135 | T | C | | 361 | I | T |
| 7 (1190) | — | — | — | M1 (248) | — | — | — |
| | 831 | A | G | BM2 (109) | 21 | M | V |

TABLE 13-continued

Mutations in B/Vienna/1/99/ca (=BV22) compared to B/Vienna/1/99/wt (BVie) 1. passage on Vero/SF

| Segment (lenght in nucleotides) | Nucleotides changed | | | Protein (length in amino acids) | Amino acids changed | | |
|---|---|---|---|---|---|---|---|
| | Position | BVie | BV22 | | Position | BVie | BV22 |
| 8 (1097) | 116 | G | A | NS1 (281) | 25 | A | T |
| | — | — | — | NS2 (122) | — | — | — |

TABLE 26

Characterization of B/Vienna/1/99 wt according to Los Alamos National Library influenza database (db) (Web-adress: www.flu.lanl.gov)

| B/Vienna/1/99 wt gene coding for | Accession Nr. amino acid seq. | Accession Nr. nucleotide seq | Remarks |
|---|---|---|---|
| PB2, segment 1 | ISDACH017 | ISDNCHB017 | in db listed as segment 2 |
| PB1, segment 2 | ISDACH016 | ISDNCHB016 | in db listed as segment 1 |
| PA, segment 3 | ISDACH015 | ISDNCHB015 | |
| HA, segment 4 | ISDACH018 | ISDNCHB018 | |
| NP, segment 5 | ISDACH013 | ISDNCHB013 | |
| NA, segment 6 | ISDACH012 | ISDNCHB012 | |
| M, segment 7 | ISDACH011 | ISDNCHB011 | |
| NS, segment 8 | ISDACH014 | ISDNCHB014 | |

In addition, further passaging of strain B/Vienna/1/99 ca for 15 additional passages (i.e. a total of 37 passages on serum-free Vero cell culture) resulted in a mutant B/Vienna/1/99 ca37 (abbreviated BV37) with properties even superior to the ones of BV22. This mutant contains an increased number of mutations vis-à-vis BV22 and appears to be the currently most promising candidate for the production of a whole-virus vaccine, particularly for an attenuated influenza live vaccine, based on a non-recombinant influenza virus mutant. The additional mutations are listed in Table 13A below:

TABLE 13 A

Mutations for BV22 and BV37 compared to B/Vienna/1/99 wt 1st passage on Vero/SF

| Segment (length in nucleotides) | Nucleotides changed | | | | Protein (length in amino acids) | Amino acids changed | | | |
|---|---|---|---|---|---|---|---|---|---|
| | Pos. | BVie | BV22 | BV37 | | Pos. | BVie | BV22 | BV37 |
| 1 (2396) | — | — | — | — | PB2 (770) | — | — | — | — |
| 2 (2369) | 594 | T | C | C | PB1 (752) | — | — | — | — |
| (BV37: 2370) | 2348 | — | — | A | | — | — | — | — |
| 3 (2305) | — | — | — | — | PA (726) | — | — | — | — |
| 4 (1882) | 457 | G | A* | A* | HA₀ (584) | 142 | A | T[+] | T[+] |
| | 1122 | C | C | A | | 363 | F | F | L |
| | 1299 | G | T | G | | 422 | K | N | K |
| | 1595 | G | A | A | | 521 | G | E | E |
| 5 (1844) | 128 | C | T | T | NP (560) | 23 | S | F | F |
| | 212 | C | C | T | | 51 | P | P | L |
| | 330 | T | C[#] | C[#] | | — | — | — | — |
| 6 (1557) | — | — | — | — | NB (100) | — | — | — | — |
| | 823 | G | A | G | NA (466) | 257 | R | Q | R |
| | 1135 | T | C* | C* | | 361 | I | T* | T* |
| 7 (1190) | 24 | G | G | A | M1 (248) | — | — | — | — |
| | 831 | A | G | G | | — | — | — | — |
| | 831 | A | G | G | BM2 | 21 | M | V | V |
| | 1029 | A | A | G | (109) | 87 | I | I | V |
| 8 (1097) | 116 | G | A | A | NS1 (281) | 25 | A | T | T |
| | — | — | — | — | NS2 (122) | — | — | — | — |

Comparison with influenza sequence database 13.2.2001 (www.flu-lanl.gov):

a) unique mutations underlined in bold type;

b) mutations common with:

*B/Lee/40, B/Osaka/70, B/Kadoma/1076/99 (resulting amino acid: I)

[+]B/Lee/40, B/Osaka/70

[#]often: B/Lee/40, B/Ann Arbor/1/66 ca & wt, B/Singapore/222/79, B/North Dakota/83, B/Norway/1/84, B/Ibaraki/2/85, B/Ann Arbor/1/86, B/Victoria/2/87, B/Aichi/5/88

*B/Kanagawa/73

It shall be understood that the influenza A and B master strains according to the present invention shall not be limited to the features and genetic characteristics explicitly listed in the tables herein but shall also comprise minor variations thereof as long as such variations are in the sense of the present invention and do not subtantially alter any one of the functional features of the virus.

Such variations may occur, for instance, due to additional steps of virus multiplication or propagation (e.g. for the purpose of obtaining material for sequence analyses).

Moreover, the gene sequences listed herein include the primer sequences (located at the beginning and at the end of each genome segment) that were used along with the present invention, which primer sequences may differ from the corresponding true sequences of the viral genome segments of either or both the wildtype and the attenuated virus strains.

EXAMPLE 5

Vaccine Safety and Efficacy

The subsequent data confirm temperature sensitivity and vaccine safety for influenza vaccines manufactured according to the present invention, e.g., as described in Example 1.

TABLE 14

Antibody response of mice after one intranasal immunisation without narcosis

| Viruses | Number of responders[1] | GMT[3] | Protection after challenge[2] |
| --- | --- | --- | --- |
| PR8/Sing ca - 2/6 | 0/6 | <4 | 5/6 |
| PR8/Sing ca - ΔNS | 4/6 | 6.7 | 5/6 |
| PR8-wt | 5/6 | 16.0 | 5/6 |

[1] number of animals with positive HI titer > 1:4
[2] number of animals without detectable virus in the lungs
[3] Geometric mean titer of antibodies in serum
PR8wt - influenza strain A/PR/8/34 wildtype (H1N1), pathogenic for mice
PR8/Sing ca-2/6 - is the reassortant between attenuated influenza strain A/Sing/1/57 ca and PR8 wt, containing 2 genes (HA and NA) from PR8wt virus and all other genes from A/Sing/1/57 ca.
PR8/Sing-ΔNS contains HA and NA genes from PR8wt, five genes from A/Sing/1/57 ca and the NS gene of PR8 origin lacking the NS1 coding sequence (NS1 deletion or knockout).

TABLE 15

Antibody response and protection of mice after intranasal immunisation with different variants of A/Singapore/1/57 virus (under narcosis)

| | Responders[1] | | | |
| --- | --- | --- | --- | --- |
| Viruses | 1-st immunisation | 2-nd immunisation | GMT after two immunisations | Protection after challenge[4] |
| A/Sing/1/57/wt va[2] | 9/9 | 9/9 | 103.9 | 9/9 |
| A/Sing/1/57/ca[3] | 8/10 | 10/10 | 55.7 | 8/10 |
| A/Sing/57/ΔNS 87 | 1/10 | 10/10 | 27.9 | 8/10 |

[1] number of animals with positive HI titer > 1:4
[2] va—Vero-adapted
[3] ca—cold-adapted
[4] number of animals without detectable virus in the lungs

TABLE 16

Reproduction of wt, va and ca variants of A/Singapore/1/57 in mouse lungs[a]

| | Virus titer in mouse lungs post infection on day, PFU/ml[b] | | |
| --- | --- | --- | --- |
| Viruses | 2 | 4 | 6 |
| A/Singapore/1/57/wt | $1.6 \times 10^6$ | $2.2 \times 10^5$ | $1.4 \times 10^3$ |
| A/Singapore/1/57/wt va | $2.5 \times 10^6$ | $2.1 \times 10^6$ | $1.0 \times 10^2$ |
| A/Singapore/1/57/ca | <10 | <10 | <10 |

[a] Mice were infected i.n. with 50 μl of virus fluid with a titer $1.0 \times 10^6$ PFU/ml.
[b] PFU/ml of 10% tissue suspension, titrated on MDCK cells.

TABLE 17

Virulence of wt and ca variants of A/Singapore/1/57 virus for ferrets

| | Number of animals with fever post infection on day | | |
| --- | --- | --- | --- |
| Viruses | 1 | 2 | 3 |
| A/Singapore/1/57 wt | FFF | NNN | NNN |
| A/Singapore/1/57 ca | NNN | NNN | NNN |

Rectal temperature of animals was recorded twice a day and characterized as follows:
N—normal temperature from 38.1° C. to 39.9° C.
F—fever, more than 40.0° C.
Each group consisted of 3 animals, which were immunized i.n. under ether narcosis with 1 ml of virus fluid with a titer of $2 \times 10^6$ PFU/ml.

TABLE 18

Reproduction of 2/6 reassortant of A/Hong Kong/1035/98 wt and A/Singapore/1/57/ca in mouse lungs[a]

| | Virus titer in mouse lungs on day 2-6 post infection, PFU/ml[b] | | |
| --- | --- | --- | --- |
| Viruses | 2 | 4 | 6 |
| A/Hong Kong/1035/98 wt H1N1 | $6.8 \times 10^4$ | $2.0 \times 10^4$ | <10 |
| A/Singapore/1/57/ca × A/Hong Kong/1035/98 wt | <10 | <10 | <10 |

[a] Mice were infected i.n. under ether narcosis with 50 μl of virus fluid.
[b] PFU/ml of 10% tissue suspension, titrated on Vero/SF cells, data are given as mean value for 6 mice (the lungs of each animal were treated separately). The reassortant contains the HA and NA genes from A/Hong Kong/1035/98 wt wildtype and the other 6 genes from A/Singapore/1/57/ca.

TABLE 19

Virulence of 6/2 reassortant of A/Vienna/47/96 wt and A/Singapore/1/57/ca for ferrets

| | Virus subtype | Number of animals with fever on day | | | Rhinitis[b] |
| --- | --- | --- | --- | --- | --- |
| Viruses | | 1 | 2 | 3 | |
| Master strain A/Singapore/1/57/ca | H2N2 | NNN | NNN | NNN | ± |
| Epidemic virus A/Vienna/47/96 wt Reassortant | H3N2 | NNN | FFF | FFF | +++ |

TABLE 19-continued

Virulence of 6/2 reassortant of A/Vienna/47/96 wt and A/Singapore/1/57/ca for ferrets

| Viruses | Virus subtype | Number of animals with fever on day | | | Rhinitis[b] |
|---|---|---|---|---|---|
| | | 1 | 2 | 3 | |
| A/Singapore/1/57/ca × Vienna/47/96 wt | H3N2 | NNN | NNN | NNN | ± |

Animals were immunized i.n. under ether narcosis with 1 ml of virus, 2 × $10^6$ PFU/ml.
N—normal temperature from 38:1° C. to 39.9° C.;
F —fever, more than 40.0° C.
[b]+++ - severe rhinitis
± absence of rhinitis The results presented in Tables 16 to 19 clearly demonstrate the safety of the vaccines containing the attenuated, temperature sensitive master strain or, in case of reassortants, of the vaccines based on the reassorted viruses composed of the "backbone" of the attenuated, temperature sensitive master strain (6 genes) and the HA and NA genes from, e.g., the pathogenic wildtype strain A/Hong Kong/1035/98 wt.

TABLE 20

Ts and ca phenotype of B/Vienna/1/99

| Virus | PFU/ml on Vero cells at | PFU/ml on MDCK cells at | |
|---|---|---|---|
| | 25° C. | 33° C. | 39° C. |
| B/Vienna/1/99 wt | <300 | $4 \times 10^6$ | $4 \times 10^5$ |
| B/Vienna/1/99 ca (BV22) | $1 \times 10^6$ | $2.4 \times 10^6$ | <20 |

TABLE 21

Genetic stability of the ts phenotype of B/Vienna/1/99 ca

| Virus | PFU/ml on MDCK cells at | |
|---|---|---|
| | 33° C. | 39° C. |
| B/Vienna/1/99 wt | $4 \times 10^6$ | $4 \times 10^5$ |
| B/Vienna/1/99 ca (BV22) | $2.4 \times 10^6$ | <20 |
| B/Vienna/1/99 ca (BV22) after 5 passages at 33° C. | $8 \times 10^5$ | <20 |

The strain BV22 was passaged five times at high MOI on Vero cells. Then the ts-phenotype was controlled again. The strain remained tmperature senssitive as can be seen in Table 21.

TABLE 22

Virulence of B/Vienna/1/99 ca and wt in mouse lungs

| Virus | organ | PFU/ml* at day post infection | | |
|---|---|---|---|---|
| | | 2 | 3 | 4 |
| B/Vienna/1/99 ca (BV22) | lung | <20 | <20 | <20 |
| | nose | $1 \times 10^2$ | $1 \times 10^2$ | 20 |
| B/Vienna/1/99 wt | lung | $8 \times 10^4$ | $7 \times 10^3$ | $4.4 \times 10^3$ |
| | nose | $3.8 \times 10^4$ | $3.4 \times 10^4$ | $1.4 \times 10^4$ |

*9 OF1 mice per strain were immunized intranasally under ether narcosis with $10^5$ PFU. At the indicated days post infection 3 mice per group were sacrificied. Lungs and nasal turbinates were homogenized for a 10% (w/v) suspension in PBS def. A plaque assay of the suspensions was performed.

The data show that moderate reproduction of the ca master strain candidate BV22 was possible in the nasal mucosa while the ts property of the virus prevented reproduction in the lungs.

TABLE 23

Ts and ca phenotype of the reassortant influenza b strain

| Virus | PFU/ml on MDCK cells at | |
|---|---|---|
| | 33° C. | 39° C. |
| B/Vienna/1/99 wt | $4 \times 10^6$ | $4 \times 10^5$ |
| B/USSR/69 wt | $1.6 \times 10^6$ | $4 \times 10^4$ |
| B/Vienna/1/99 ca (BV22) | $1.4 \times 10^6$ | <20 |
| BV22 × B/USSR/69 (6/2) | $8 \times 10^6$ | <20 |

A 6/2 reassortant strain containing HA and NA of the wild type influenza strain B/USSR/69 wt and the other 6 genome segments from B/Vienna/1/99 ca (BV22) was established. The origin of the hemagglutinin was tested by HI-assay, all other genome segments by RT-PCT and restriction analysis using methods known in the art.

TABLE 24

Virulence of the reassortant influenza B strain in mouse lungs

| Virus | organ | PFU/ml* at day post infection | | |
|---|---|---|---|---|
| | | 2 | 3 | 4 |
| B/Vienna/1/99 ca (BV22) | lung | <20 | <20 | <20 |
| | nose | <20 | $1 \times 10^2$ | 40 |
| B/USSR/69 wt | lung | $1.8 \times 10^5$ | $4 \times 10^5$ | $2.4 \times 10^4$ |
| | nose | $1.6 \times 10^5$ | $2 \times 10^5$ | $1.6 \times 10^5$ |
| BV22 × B/USSR/69 wt (6/2) | lung | <20 | <20 | <20 |
| | nose | $2.8 \times 10^3$ | $2 \times 10^3$ | $4 \times 10^2$ |

*9 OF1 mice per strain were immunized intranasally under ether narcosis with $10^5$ PFU. At the indicated days post infection 3 mice per group were sacrificied. Lungs and nasal turbinates were homogenized for a 10% (w/v) suspension in PBS def. A plaque assay of the suspensions was performed.

EXAMPLE 6

Clinical Study

The following vaccines (in the form of nasal sprays) were produced according to the present invention (e.g. as described in Example 1) for intranasal delivery. Composition per ml (after reconstitution of freeze-dried material):

(1) Placebo: 2× SF-medium, 40 mM HEPES buffer, 8% lactalbumin enzymatic hydrolysate, 4% trehalose;

(2) Vero-Vac H1: A/Beijing/262/95 (H1N1)-like preparation comprising $4.3 \times 10^7$ TCID$_{50}$ of 6/2 reassortant A/Singapore/1/57/ca with A/Hong Kong/1035/98; 2× culture supernatant, 40 mM HEPES buffer, 8% lactalbumin enzymatic hydrolysate, 4% trehalose;

(3) Vero Vac H3: A/Sidney/5/97 (H3N2)-like preparation comprising $2.1 \times 10^7$ TCID$_{50}$ of 6/2 reassortant A/Singapore/1/57/ca with A/SW/7729/98; 2× culture supernatant, 40 mM HEPES buffer, 8% lactalbumin enzymatic hydrolysate, 4% trehalose;

(4) Russian trivalent vaccine (live influenza vaccine for adults):

| | | |
|---|---|---|
| A/17/Beijing/95/25 (H1N1) | $1.1 \times 10^8$ | $EID_{50}$ |
| A/17/Sidney/97/76 (H3N2) | $2.3 \times 10^7$ | $EID_{50}$ |
| B/60/Petersburg/95/20 | $1.1 \times 10^7$ | $EID_{50}$ |

(5) Monovalent Vero vaccine BV22: B/Beijing/184/93—like preparation comprising $2 \times 10^6$ $TCID_{50}$ of master strain candidate B/Vienna/1/99/ca (=BV22); 2× culture supernatant, 40 mM HEPES buffer, 8% lactalbumin enzymatic hydrolysate, 4% trehalose;

The vaccines were administrated to 13 volunteers per each vaccination group. 550 μl of reconstituted vaccine (or placebo, respectively) were given intranasally to each patient on day 0 and for a second time on day 22±1. The results are summarized in Table 25 below.

Safety Results:

The total number of adverse events (AE) during five days after the first and second vaccination was 14 including 9 mild and 4 moderate AE. Only one volunteer showed severe AE, comprising an increase in body temperature up to 38.8° C. within 3 hours after the first vaccination without any local or systemic symptoms. During the next four hours his temperature became normal again. After the first vaccinations 7 AE were observed, One of them was local and six were systemic. After the second vaccination 2 local and 5 systemic AE were observed.

No significant difference in terms of safety was revealed between the groups of the study including the one with placebo. No serious AE related to the vaccination were observed except for the one mentioned above. Two of the moderate AE occurred in the H3N2 group (temperature elevation up to 37.6° and acute pharyngitis on day 3 in one volunteer; nasal obstruction, discomfort in the throat on day 22-24 and temperature elevation up to 37.5° C. in another volunteer), and one in the H1N1 group (pain in the throat, rhinitis from day 22-26, temperature elevation up to 37-37.8° C. between days 22-24).

TABLE 25

Response of seronegative volunteers to Vero Vac vaccines and to a trivalent Russian cold-adapted egg derived vaccine

| | | | | % of volunteers with at least 4-fold increase of serum HAI antibody titre to antigens | | |
|---|---|---|---|---|---|---|
| No | Vaccine for immunization | Virus dose, $TCID_{50}/ml$ or $EID_{50}/ml$ | No. of volunteers | H1N1 | H3N2 | B |
| 1 | Placebo | | 13 | | (8) | |
| 2 | Vero Vac H1 (H1N1) | $4.3 \times 10^7$ | 13 | 38 | | |
| 3 | Vero Vac H3 (H3N2) | $2.1 \times 10^7$ | 13 | | 67 | |
| 4 | Russian trivalent vaccine: | | 13 | | | |
| | A/17/Beijing/95/25 H1N1 | $1.1 \times 10^8$ | | 46 | | |
| | A/17/Sidney/97/76 H3N2 | $2.3 \times 10^7$ | | | 8 | |
| | B/60/Petersburg/95/20 | $1.1 \times 10^7$ | | | | 31 |
| 5 | Vero vaccine BV22 | $2 \times 10^6$ | 13 | | | 33 |

(8) patient developed spontaneous infection during course of study.

The results obtained from the clinical study thus confirm a very good safety of the vaccines produced according to the present invention and using the preferred influenza A and B master strain candidates of the present invention.

We claim:

1. A whole-virus vaccine in the form of an attenuated influenza live vaccine, comprising at least one influenza virus selected from the group consisting of strain A/Sing/1/57ca, strain A/Sing/1/57ca/ΔNS 87, strain A/Sing/1/57ca/ΔNSPR8, strain A/Sing/1/57ca/NS124PR8, strain B/Vienna/1/99ca, strain B/Vienna/1/99ca37, and a reassortant strain, the reassortant strain being composed of a backbone of five or six influenza genome segments from one of the foregoing strains encoding proteins other than HA and NA; and of a HA genome segment and a NA genome segment from an influenza wildtype strain.

2. The vaccine according to claim 1 wherein it selectively agglutinates human erythrocytes but not chicken erythrocytes.

3. The vaccine according to claim 1, wherein the backbone consists of five of said genome segments.

4. The vaccine according to claim 1, wherein the backbone consists of six of said genome segments.

* * * * *